United States Patent [19]  [11] Patent Number: 4,794,073
Dattagupta et al.  [45] Date of Patent: Dec. 27, 1988

[54] DETECTION OF NUCLEIC ACID HYBRIDS BY PROLONGED CHEMILUMINESCENCE

[75] Inventors: Nanibhushan Dattagupta, New Haven, Conn.; Anton H. Clemens, Elkhart, Ind.

[73] Assignee: Molecular Diagnostics, Inc., West Haven, Conn.

[21] Appl. No.: 753,734

[22] Filed: Jul. 10, 1985

[51] Int. Cl.⁴ .................. C12Q 1/68; C07H 21/00
[52] U.S. Cl. ........................... 435/6; 435/28; 536/27; 252/700
[58] Field of Search ............... 435/6, 28; 536/27; 252/700

[56] References Cited

U.S. PATENT DOCUMENTS

| 4,563,417 | 1/1986 | Albarella | 435/6 |
| 4,598,044 | 7/1986 | Kricka | 435/28 |
| 4,617,261 | 10/1986 | Sheldon, III | 435/7 |
| 4,623,627 | 11/1986 | Huang | 435/6 |
| 4,629,689 | 12/1986 | Diamond | 435/6 |

FOREIGN PATENT DOCUMENTS

| 0070687 | 1/1983 | European Pat. Off. |
| 0087959 | 9/1983 | European Pat. Off. |
| 0103784 | 6/1984 | European Pat. Off. |
| 0116454 | 8/1984 | European Pat. Off. |
| 0157629 | 10/1985 | European Pat. Off. |
| 8200479 | 1/1982 | Sweden |
| 2162946 | 8/1985 | United Kingdom |
| 8303104 | 9/1983 | World Int. Prop. O. ............ 435/28 |

OTHER PUBLICATIONS

Matthews, Anal. Biochem. 151(1) p. 205, 1985.
Gary H. G. Thorpe, Robert Haggart, Larry J. Kricka and Thomas P. Whitehead, "Enhanced Luminescent Enzyme Immunoassays for Rubella Antibody, Immunoglobin and Digoxin", Biochemical and Biophysical Research Communications, vol. 119, No. 2, pp. 481–487, Mar. 15, 1984.
Thomas P. Whitehead, Gary H. G. Thorpe, Timothy J. N. Carter, Carol Groucutt and Larry J. Kricke, "Enhanced Luminescence Procedure for Sensitive Determination of Peroxidase-labelled Conjugates in Immunoassay", Nature, vol. 305, pp. 158–159, Sep. 8, 1983.
Photochemistry Photobiology, vol. 40, pp. 823–830, (1984).
CA. vol. 59, No. 12, 9.12.63 1963 Columbus, Ohio, U.S.A., 14249b, 57-Enzymes, The Stimulation of Horseradish Peroxidase by Nitrogenous Ligands.
30 Chemical Abstracts, published by American Chemical Society, vol. 103, No. 25, Dec. 23–Dec. 30, 1985, CHABA 8, Columbus, Ohio, Abstract No. 103: 210409m.

Primary Examiner—Robert J. Warden
Assistant Examiner—Robert Benson
Attorney, Agent, or Firm—Sprung Horn Kramer & Woods

[57] ABSTRACT

A nucleic acid probe capable of participating in a chemiluminescent reaction comprising a defined nucleic acid sequence, the sequence being linked to any one of
a. a chemiluminescence precursor,
b. a chemiluminescence enhancer, and
c. an enzyme the remaining two of (a), (b) and (c) not linked to the sequence being in a mixture of the linked sequence. A method for determining a particular single stranded polynucleotide sequence in a test medium, comprising the steps of:
(a) combining the test medium with a polynucleotide probe having a base sequence substantially complementary to the sequence to be determined,
(b) labeling either the resulting hybrids or probe which has not hybridized with the sequence to be determined with one of the participants in an enhanced chamiluminescent reaction involving a chemiluminescent precursor, an enzyme, an oxidant, and a chemiluminescence enhancer,
(c) initiating such chemiluminent reaction with the labeled hybrid or probe, and
(d) detecting the resulting light emission.

5 Claims, 10 Drawing Sheets

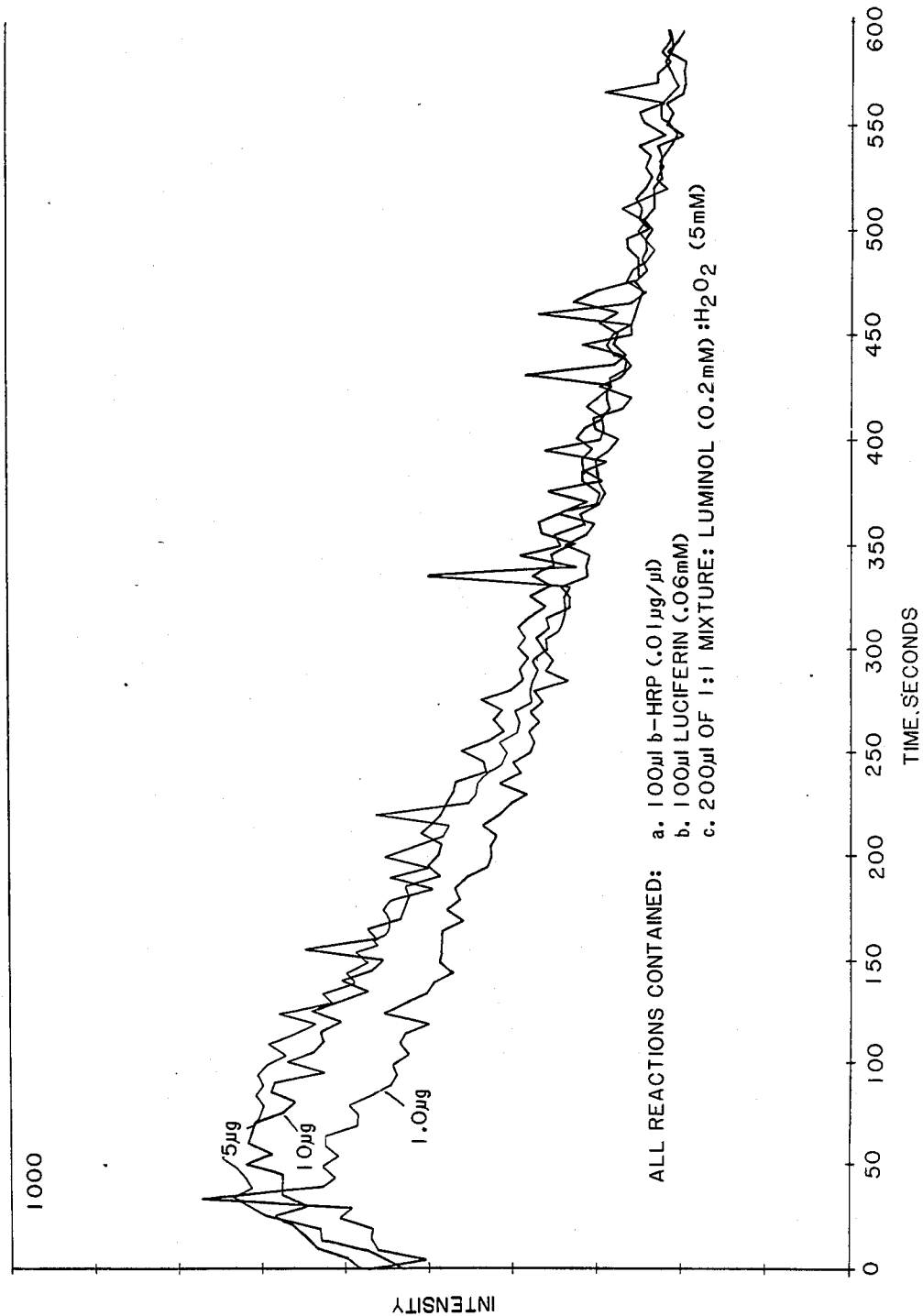

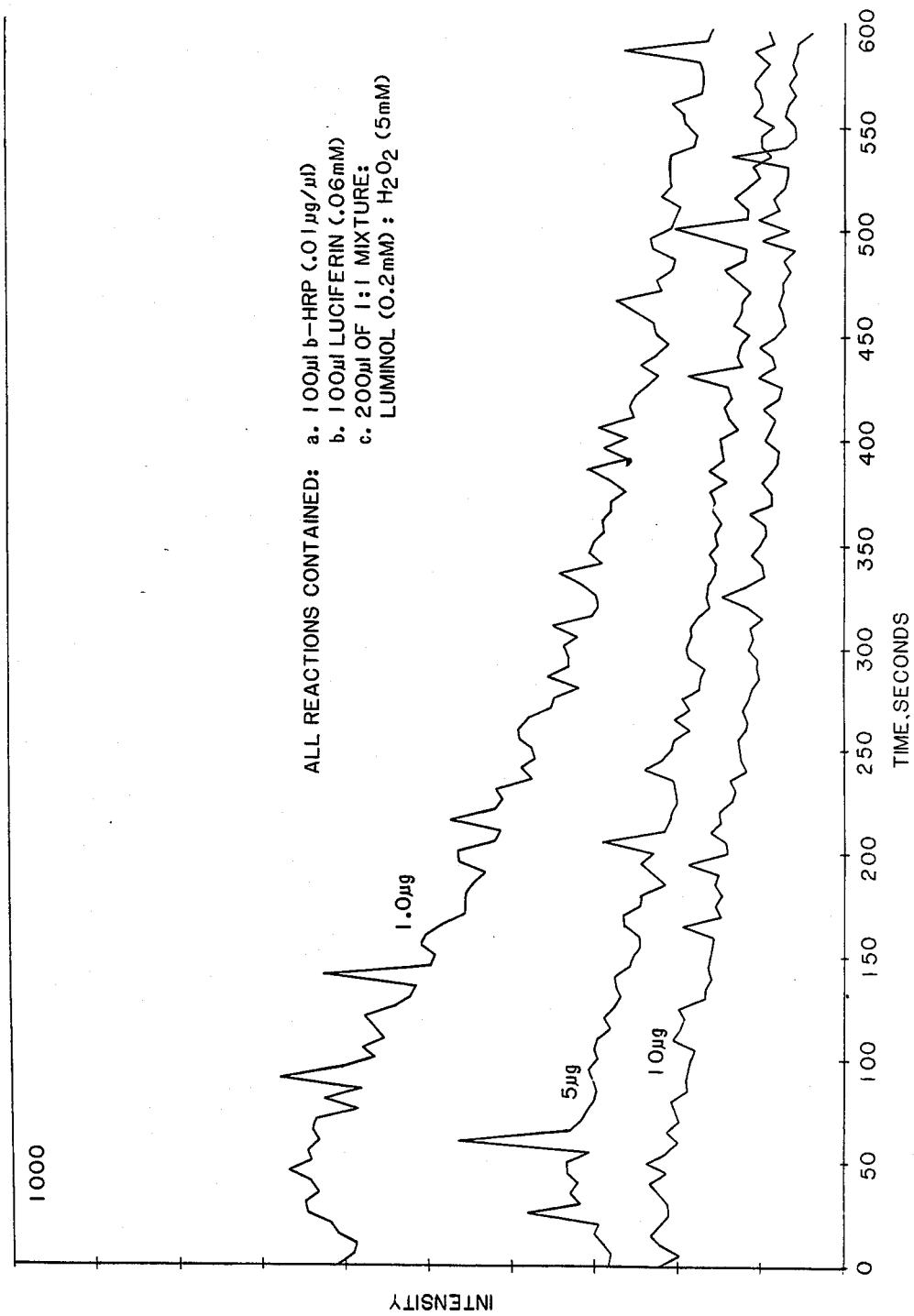

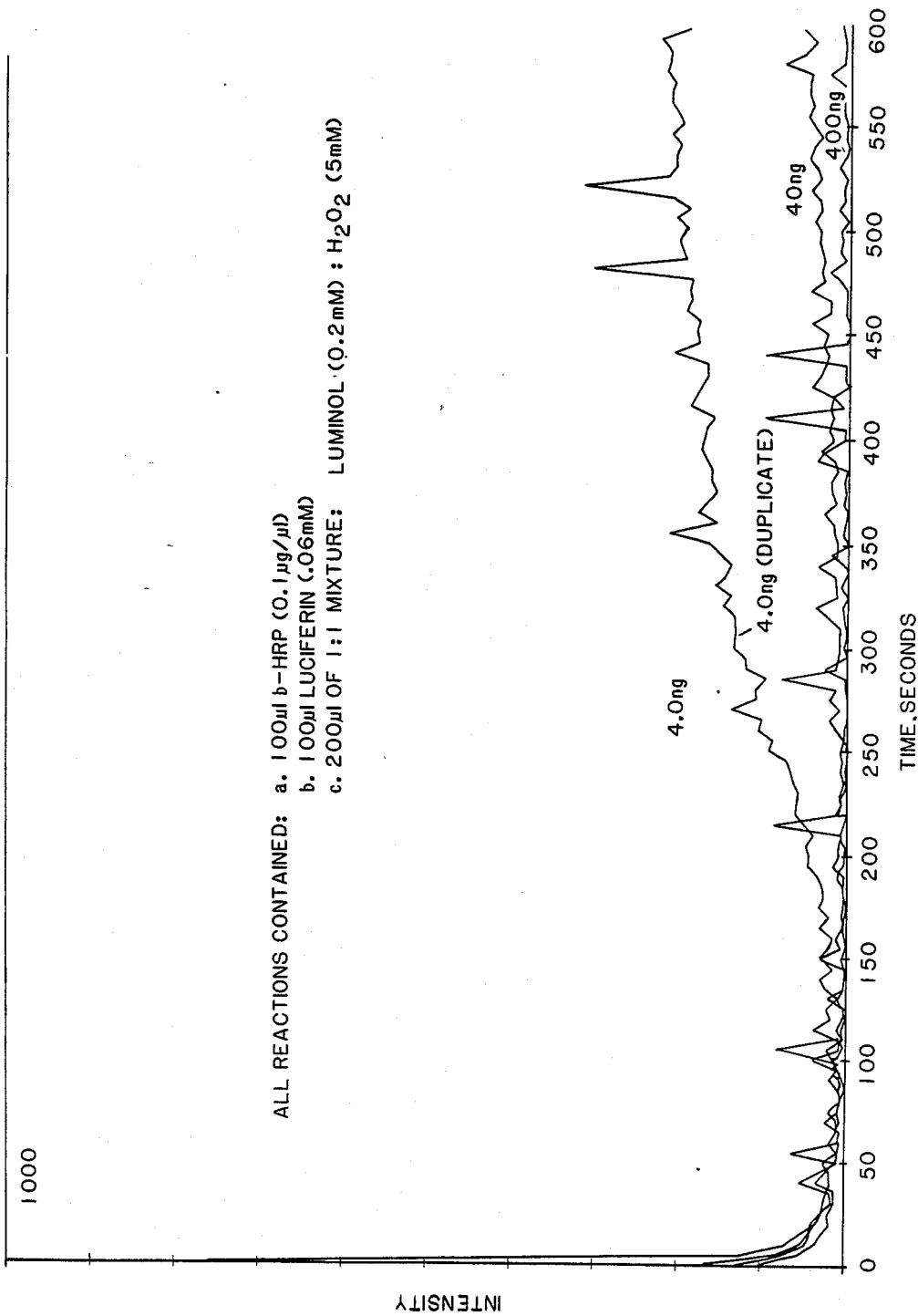

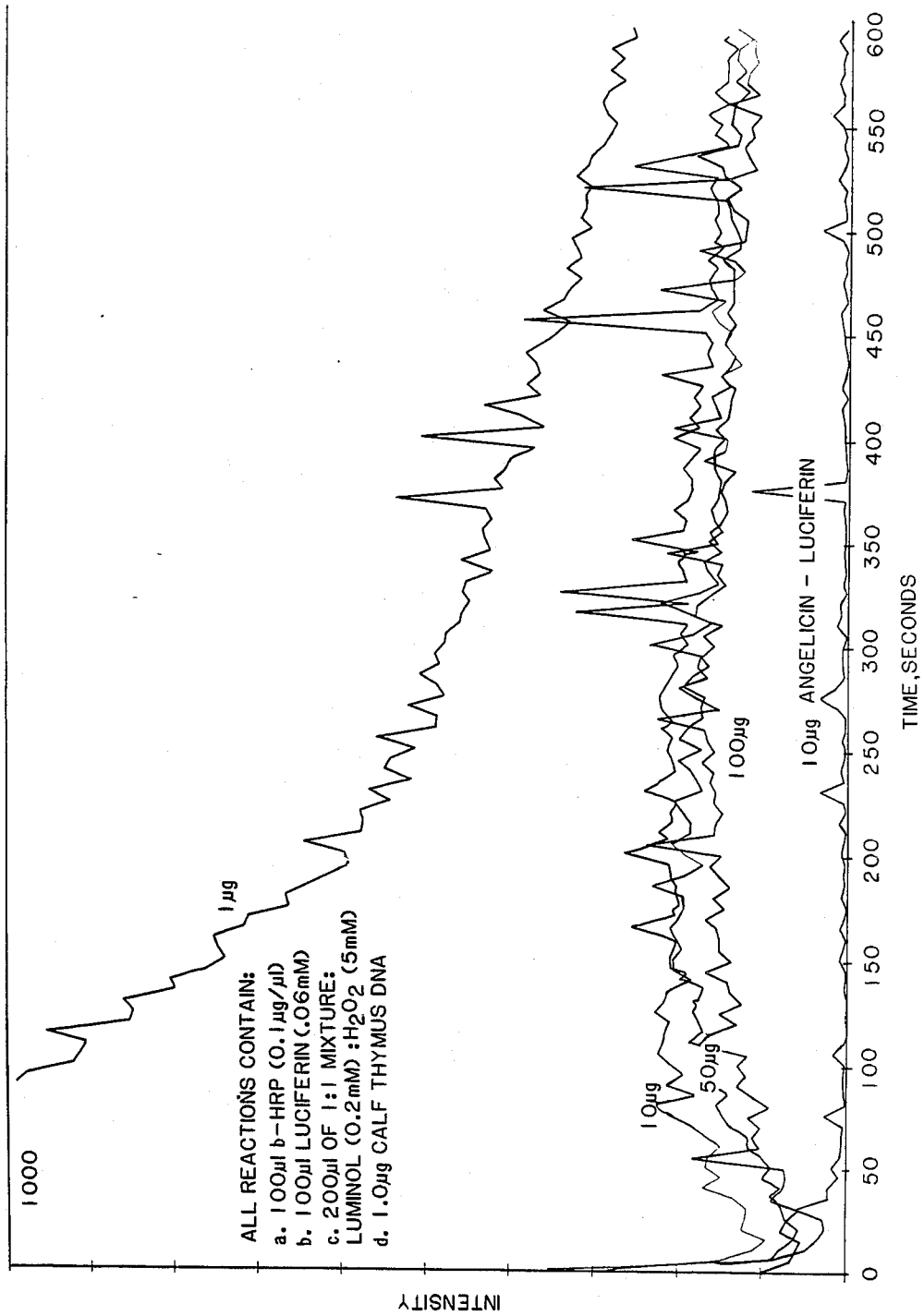

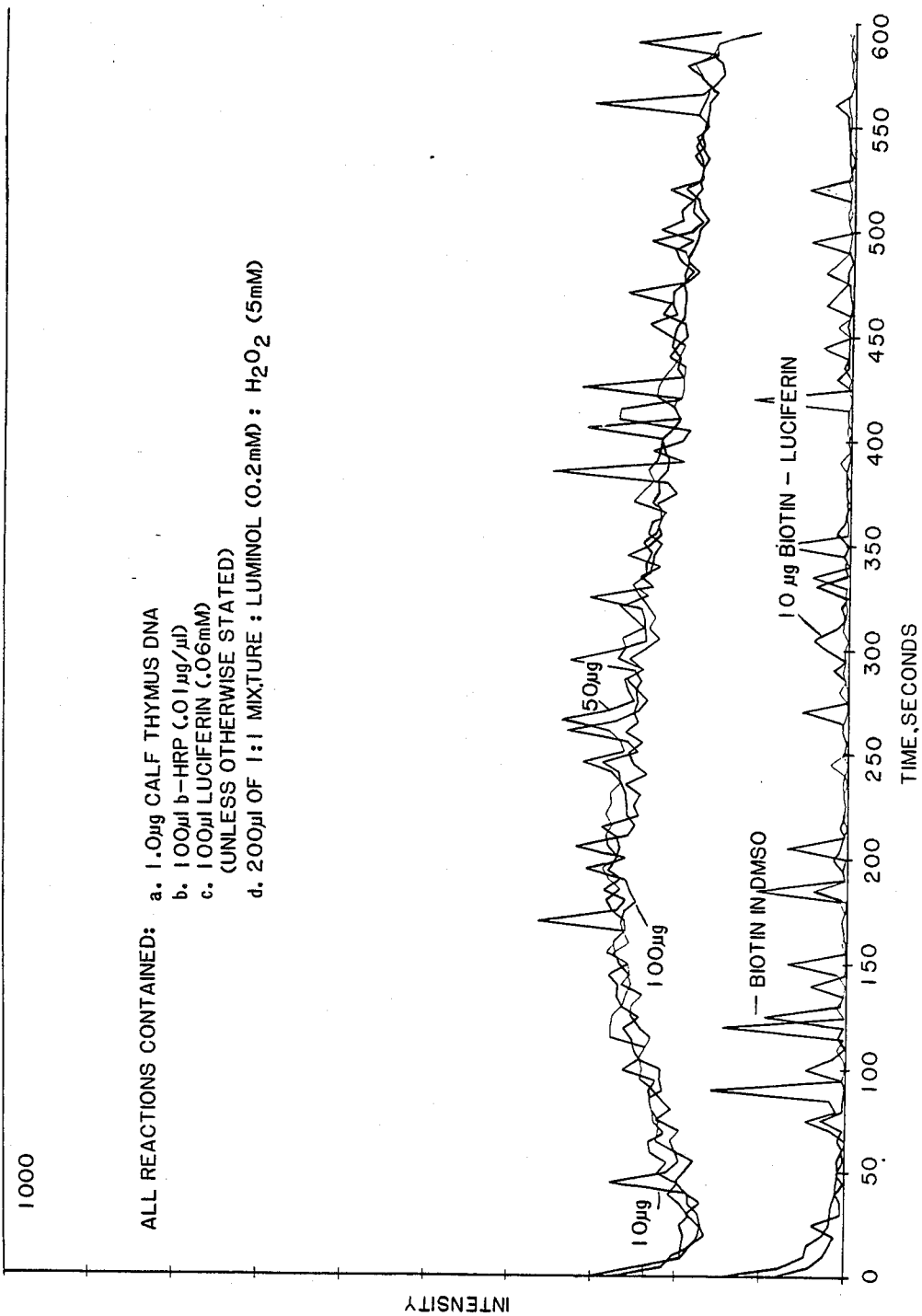

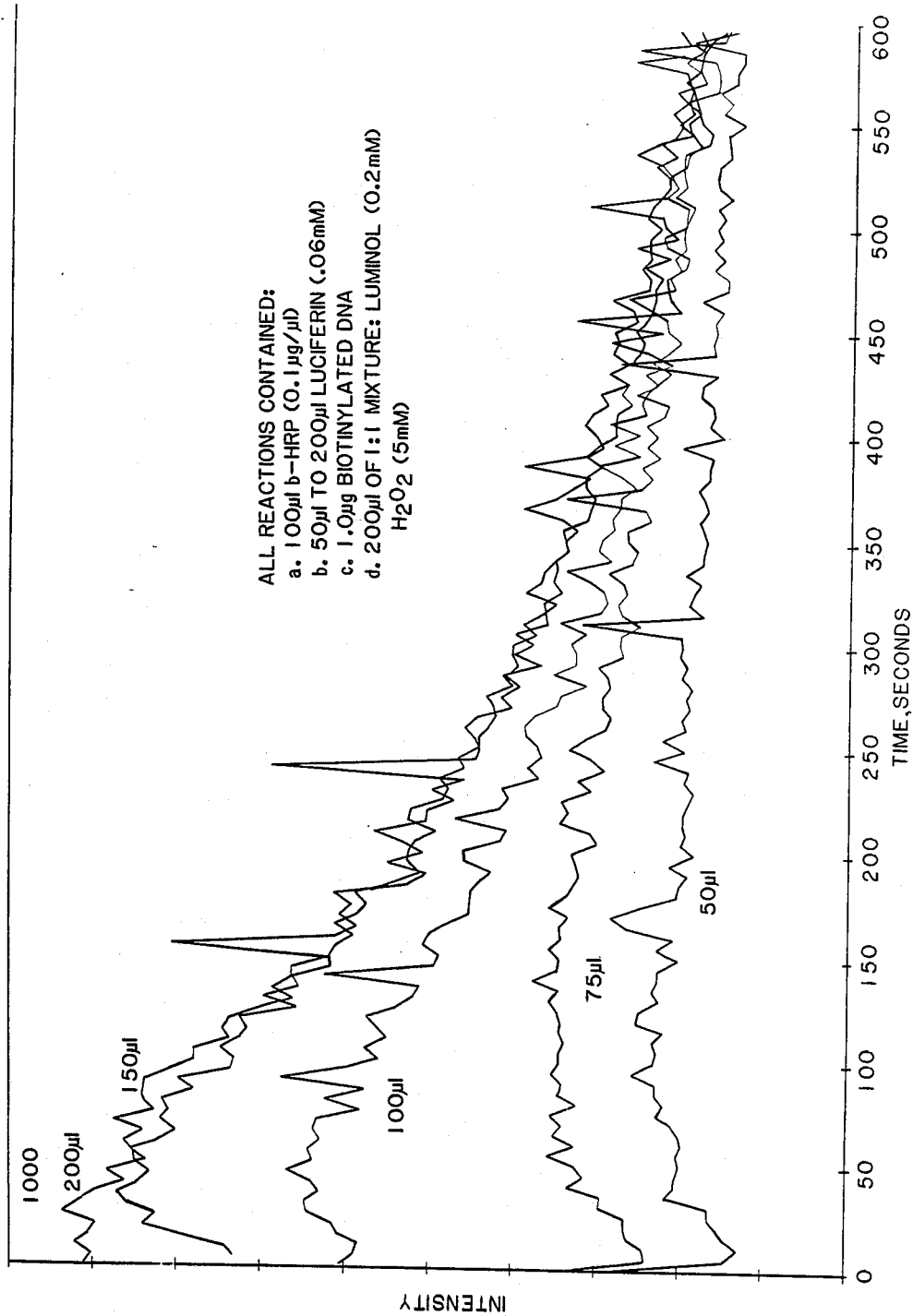

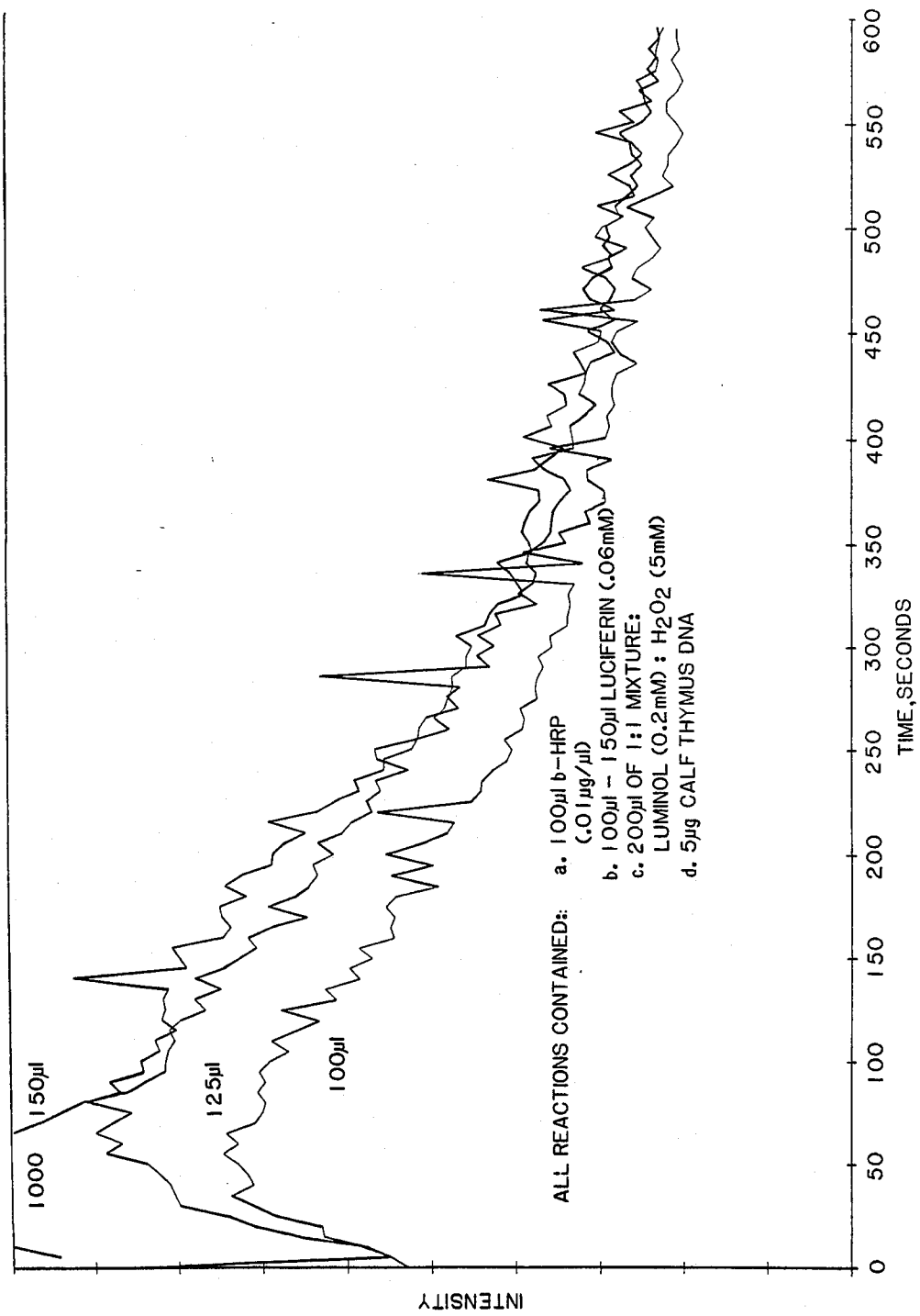

UNBIOTINYLATED ADENOVIRUS DNA vs. BIOTINYLATED ADENOVIRUS DNA:

DETECTION LIMITS

UNBIOTINYLATED ADENOVIRUS DNA

100ng        1 pg

BLANK

BLANK

100ng        1 pg

BIOTINYLATED ADENOVIRUS DNA
(30-60 SECOND REACTION TIME)

DETECTION OF HYBRIDIZED ADENOVIRUS DNA 1 pg AND BLANK 1 ug  10pg

HYBRIDIZED ADENOVIRUS DNA
(30-60 SECOND REACTION TIME)

DETECTION OF HYBRIDIZED PBR322 DNA 1 pg AND BLANK 1 ug           10 pg

HYBRIDIZED PBR322 DNA
(30-60 SECOND REACTION TIME)

DETECTION OF NUCLEIC ACID HYBRIDS BY PROLONGED CHEMILUMINESCENCE

BACKGROUND OF THE INVENTION

The present invention relates to the detection of a nucleic acid hybrid by chemiluminescent reactions. It is known that chemiluminescent detection is one of the most sensitive ways of detecting an analyte. The process, although sensitive, suffers from several disadvantages. In most cases the chemiluminescent reaction mediated emission of light has a very short lifetime, i.e., light emission is very quick, so that a sophisticated device has to be developed to monitor the extent of light emission and also to determine the extent of the presence of an analyte. It is also difficult to couple the interacting systems to the analyte without destroying or changing the property of the interacting partners.

Recently, it has been demonstrated that if a substance, for example, an iodophenol or a benzothiazole derivative is present during the chemiluminescent emission mediated by horseradish peroxidase, the reaction rate is retarded and simultaneously the quantum yield of the light emission is enhanced (European Patent Application No. 0 116 454; European Patent Application No. 0 103 784; UK Patent Application No. 820 62 63; Gary H. G. Thorpe, Robert Haggart, Larry J. Kricka and Thomas P. Whitehead, "Enhanced Luminescent Enzyme Immunoassays For Rubella Antibody, Immunoglobulin And Digoxin", *Biochemical and Biophysical Research Communications*, Vol. 119, No. 2, pp. 481–487, March 15, 1984; Thomas P. Whitehead, Gary H. G. Thorpe, Timothy J. N. Carter, Carol Groucutt and Larry J. Kricka, "Enhanced Luminescence Procedure For Sensitive Determination Of Peroxidase-labelled Conjugates In Immunoassay", *Nature*, Vol. 305, pp. 158–159, Sept. 8, 1933; Gary H. G. Thorpe, Larry J. Kricka, Eileen Gillespie, Susan Mosely, Robert Amess, Neil Baggett and Thomas P. Whitehead, "Enhancement Of The Horseradish Peroxidase Catalysed Chemiluminescent Oxidation Of Cyclic Diacyl Hydrazides By 6-Hydroxybenzothiazoles", *Anal. Biochem.*). Although this method has been shown to be useful in the detection of an analyte by conventional immunoassay methods, it has never been demonstrated, however, whether this method could be utilized to detect a nucleic acid hybrid.

It has been demonstrated heretofore that a chemiluminescent reaction occurs where the emission is due to an iron initiated activation of bleomycin. The self-inactivation reaction is affected by the presence of DNA.

In *Photochemistry Photobiology*, Vol. 40, pg 823–830, (1984), it was described that photoemission is quenched by target molecules such as DNA and that the presence of DNA does not prevent the iron-initiated activation of bleomycin, by the so-called self-inactivation reaction associated with chemiluminescence. The article went on to state that these findings seem to suggest that an electronically excited intermediate of bleomycin can alter bio-molecules though, in that case, the nature of the excited state was not precise. Swedish patent application No. 8200479 describes chemiluminescent detection of nucleic acid hybrids. European patent application No. 0 070 687 concerns a light-emitting polynucleotide hybridization diagnostic method.

SUMMARY OF THE INVENTION

It is an object of the present invention to provide nucleic acids capable of participating in a chemiluminescent reaction.

It is another object of the invention to provide methods of detecting nucleic acids in unknown samples.

It is a further object of the invention to detect nucleic acid hybrids.

These and other objects are realized by the present invention.

The present invention concerns a nucleic acid probe capable of participating in a chemiluminescent reaction comprising
a. a defindd nucleic acid sequence, and
b. a chemiluminescence precursor photochemically linked to the nucleic acid sequence.

Another nucleic acid probe according to the present invention comprises
a. a defined nucleic acid sequence, and
b. a chemiluminescence enhancer linked, for example, covalently linked, to the nucleic acid sequence. Such probe can be used as a participant in an enhanced chemiluminescent reaction and also as a substrate for luciferase type enzymes. The probe, i.e., substrate, can be linked to the enzyme by a photochemical linker.

The present invention also concerns a further nucleic acid probe capable of participating in an enhanced chemiluminescent reaction comprising a defined nucleic acid sequence, the sequence being linked to any one of
a. a chemiluminescence precursor,
b. a chemiluminescence enhancer, and
c. an enzyme, the remaining two of (a), (b) and (c) not linked to said sequence, being in a mixture with the linked sequence. The nucleic acid probe can exist as a homogeneous mixture, e.g., solution, a heterogeneous phase or in a hybridized form. The hybridized form can exist as a homogeneous mixture, e.g., solution, or as a heterogeneous phase.

The present invention also concerns a method for determining a particular single stranded polynucleotide sequence, e.g., by hybridization, in a test medium, comprising the steps of:

(a) combining the test medium with a polynucleotide probe having a base sequence substantially complementary to the sequence to be determined under conditions favorable to hybridization between the probe and the sequence to be determined, (b) labeling either the resulting hybrids or probe which have not hybridized with the sequence to be determined with one of the participants in an enhanced chemiluminescent reaction involving a chemiluminescent precursor, an enzyme, an oxidant, and a chemiluminescence enhance, (c) initiating such chemiluminent reaction with the labeled hybrids or probe, and (d) detecting the resulting light emission.

The present invention concerns another method for determining a particular single stranded polynucleotide sequence in a test medium, comprising the steps of:

(a) immobilizing single stranded nucleic acids in the test medium, (b) contacting the immobilized nucleic acids with a polynucleotide probe having a base sequence substantially complementary to the sequence to be determined under conditions favorable to hybridization between the probe and the sequence to be determined,
wherein the probe (1) is labeled with a chemiluminescence label selected from the participants in an enhanced chemiluminescent reaction involving a 2,3-dihydro-1,4-phthalazinedione chemiluminescent precursor, a peroxidase enzyme and a chemiluminescence enhancer, or (2) comprises a binding site for a specific binding partner, (c) separating resulting immobilized hybrids from probe which have not hybridized with the sequence to be determined, and where the probe comprises the binding site, adding the binding partner which is labeled with the chemiluminescence label, (d) initiating the chemiluminescent reaction with the separated, labeled, immobilized hybrids, and (e) detecting the resulting light emission.

The present invention also relates to a further method for determining a particular single stranded polynucleotide sequence in a test medium, comprising the steps of:

(a) combining the test medium with a polynucleotide probe having a base sequence substantially complementary to the sequence to be determined to form hybrids having an antigenic determinant which distinguish them from single stranded nucleic acids, wherein the probe is either in an immobilized form or comprises a binding site whereby the probe is immobilizable by contact with an immobilized form of a binding partner for such binding site, (b) when the probe is in the immobilizable form, contacting the resulting hybrids with the immobilized binding partner, (c) contacting the resulting immobilized hybrids with an antibody reagent capable of binding to the distinguishing antigenic determinant, which antibody reagent is labeled with one of the participants in an enhanced chemiluminescent reaction involving a 2,3-dihydro-1,4-phthalazinedione chemiluminescent precursor, a peroxidase enzyme and a chemiluminescence enhancer, (d) separating into fractions the labeled antibody reagent that becomes bound to immobilized hybrids from that which does not bind, (e) initiating the chemiluminescent reaction in one of the separated fractions, and (f) detecting the resulting light emission.

The present invention is also directed to processes for detecting a nucleic acid hybrid.

In one process according to the present invention for detecting a nucleic acid hybrid an unknown nucleic acid-containing sample is contacted in a mixture, for example, a solution, with a probe comprising a defined nucleic acid sequence and a chemiluminescence precursor linked to the nucleic acid sequence and thereafter adding a chemiluminescence enhancer and an oxidant and then determining the extent of light emission.

In another process according to the present invention for detecting a nucleic acid hybrid, an unknown nucleic acid-containing sample is contacted in a mixture, for example, a solution, with a probe comprising a defined nucleic acid sequence and a chemiluminescence enhancer linked to the nucleic acid sequence and thereafter adding a chemiluminescence precursor and an oxidant and then determining the extent of light emission.

A further process for detecting a nucleic acid hybrid according to the present invention involves contacting in a mixture, for example, a solution, an unknown nucleic acid-containing sample with a probe, such probe comprising a. a defined nucleic acid sequence, b. a photochemical linker bound to the nucleic acid sequence, c. a ligand bound to the linker, d. a binding protein bound to the ligand, and e. an enzyme bound to the binding protein, and thereafter adding a chemiluminescence substance, a chemiluminescence enhancer and an oxidant, and then determining the extent of light emission.

Subpicogram amounts of nucleic acid hybrids can be detected by the present invention, whereas for immunoassays using chemiluminescence techniques only nanogram quantities of the analyte, i.e., antibody or antigen, can be reliably detected.

The present invention is based on the surprising observation that under certain conditions nucleic acids do not have an appreciable effect on the process, so that enzyme, for example, horseradish peroxidase, mediated chemiluminescent reactions can be utilized to detect the presence of very small amounts of DNA, RNA or any other nucleic acid after the nucleic acid has been hybridized to the corresponding unknown test sample or to the complementary nucleic acid sequences.

BRIEF DESCRIPTION OF THE DRAWINGS

FIG. 1 shows the effects of calf thymus DNA on rate of light emission.

FIG. 2 shows the effects of biotinylated DNA on the rate of light emission.

FIG. 3 shows the effects of nick-translated biotinylated DNA on the rate of light emission.

FIG. 4 shows the effects of angelicin on the rate of light emission.

FIG. 5 shows the effects of biotin on the rate of light emission.

FIG. 6A shows the effects of luciferin with biotinylated DNA on the rate of light emission.

FIG. 6B shows the effects of luciferin with unbiotinylated DNA on the rate of light emission.

DETAILED DESCRIPTION OF THE INVENTION

Figure 7:
FIG. 7 depicts the detection limits of unbiotinylated Adenovirus DNA vs. biotinylated Adenovirus DNA.
Figure 8:
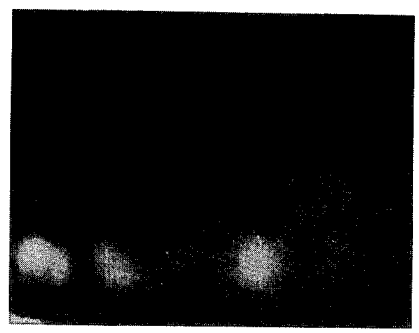
FIG. 8 depicts the detection of hybridized biotinylated Adenovirus DNA.
Figure 9:
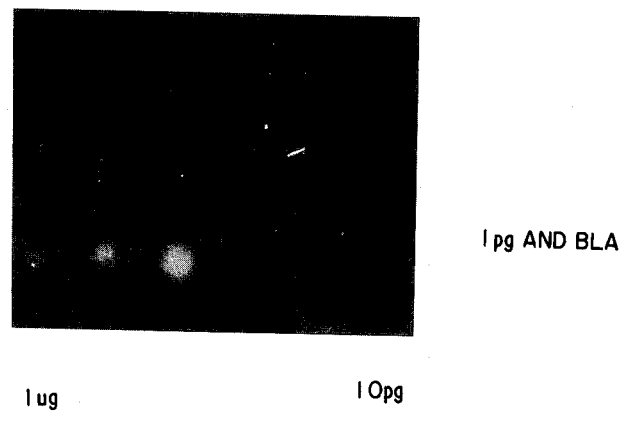
FIG. 9 depicts the detection of hybridized biotinylated PBR 322 DNA.

Non-limiting examples of nucleic acid sequences for use in the present invention can be singly or doubly stranded DNA or RNA or fragments thereof, such as are produced by restriction enzymes or even relatively short oligomers.

One nucleic acid probe for use in the process of the present invention comprises a nucleic acid sequence bound to a ligand, such ligand bound to a binding protein and such binding protein bound to an enzyme. The nucleic acid sequence can be bound to the ligand by an intercalator compound such as a furocourmarin or a phenanthridine compound, or by a non-intercalator compound such as netropsin, distamycin and bis-benzimidazole. Particularly preferred intercalator compounds are furocourmarins, for examlle, angelicin (isopsoralen), psoralen and derivatives thereof, e.g., 4-aminomethyl-4-5'-dimethyl angelicin, 4'-aminomethyltrioxsalen, 3-carboxy-5- or -8-amino- or -hydroxy- psoralen, as well as mono- or bi-azido aminoalkyl methidium or ethidium compounds.

Non-limiting examples of intercalating agents for use in the present invention are exemplified in the following Table:

TABLE

| Intercalator Classes and Representative Compounds | Literature References |
| --- | --- |
| A. Acridine dyes | J. Lerman, Mol. Biol., 3, 18 (1961); Bloomfield et al, Physical Chemistry of Nucleic Acids, Chapter 7, pp. 429–476, Harper and Rowe, NY (1974); |
| proflavin, acridine orange, quinacrine, acriflavine | Miller et al, Biopolymers, 19, 2091 (1980) |
| B. Phenanthridines | Bloomfield et al, supra Miller et al, supra |
| ethidium coralyne | Wilson et al, J. Med. Chem., 19, 1261 (1976) |
| ellipticine, ellipticine cation and derivatives | Festy et al, FEBS Letters, 17, 321 (1971); Kohn et al, Cancer Res., 35, 71 (1976); LePecq et al, PNAS (USA), 71 5078 (1974); Pelaprat et al, J. Med. Chem., 23, 1330 (1980) |
| C. Phenazines 5-methylphenazine cation | Bloomfield et al, supra |
| D. Phenothiazines chlopromazine | ibid |
| E. Quinolines chloroquine quinine | ibid |
| F. Aflatoxin | ibid |
| G. Polycyclic hydrocarbons and their oxirane derivatives | ibid |
| 3,4-benzpyrene benzopyrene diol epoxide, 1-pyrenyl-oxirane | Yang et al, Biochem. Biophys. Res. Comm., 82, 929 (1978) |
| benzanthracene-5,6-oxide | Amea et al, Science, 176, 47 (1972) |
| H. Actinomycins actinomycin D | Bloomfield et al, supra |
| I. Anthracyclinones beta-rhodomycin A daunamycin | ibid |
| J. Thiaxanthenones miracil D | ibid |
| K. Anthramycin | ibid |
| L. Mitomycin | Ogawa et al, Nucl. Acids Res., Spec. Publ. 3, 79 (1977); Akhtar et al, Can. J. Chem., 53, 2891 (1975) |
| M. Platinium Complexes | Lippard, Accts. Chem. Res., 11, 211 (1978 |
| N. Polyintercalators echinomycin | Waring et al, Nature, 252, 653 (1974); Wakelin, Biochem. J., 157, 721 (1976) |
| quinomycin triostin BBM928A tandem | Lee et al, Biochem. J., 173, 115 (1978); Huang et al, Biochem, 19, 5537 (1980); Viswamitra et al, Nature, 289, 817 (1981) |
| diacridines | LePecq et al, PNAS (USA), 72, 2915 (1975); Carrellakis et al, Biochem. Biophys. Acta, 418, 277 (1976); Wakelin et al, Biochem, 17, 5057 (1978); Wakelin et al, FEBS Lett., 104, 261 (1979); Capelle et al, Biochem., 18, 3354 (1979); Wright et al, Biochem., 19, 5825 (1980); Bernier et al, Biochem. J., 199, 479 (1981); King et al, Biochem., 21, 4982 (1982) |
| ethidium dimer | Gaugain et al, Biochem., 17, 5078 (1978); Kuhlman et al, Nucl. Acids Res. 5, 2629 (1978); Marlcovits et al, Anal. Biochem., 94, 259 (1979); Dervan et al, JACS, 100, 1968 (1978); ibid 101, 3664 (1979) |
| ellipticene dimers and analogs | Debarre et al, Compt. Rend. Ser. D., 284, 81 (1977); Pelaprat et al, J. Med. Chem., 23, 1336 (1980) |
| heterodimers | Cain et al, J. Med. Chem., 21, 658 (1978); Gaugain et al, Biochem., 17, 5078 (1978) |
| trimers | Hansen et al, JCS Chem. Comm., 162 (1983); Atnell et al, JACS, 105, 2913 (1983) |
| O. Norphillin A | Loun et al, JACS, 104, 3213 (1982) |
| P. Fluorenes and fluorenones | Bloomfield et al, supra |
| fluorenodiamines | Witkowski et al, Wiss. Beitr.-Martin-Luther-Univ. Halee Wittenberg, 11 (1981) |
| Q. Furocoumarins angelicin | Venema et al, MGG, Mol. Gen. Genet., 179, 1 (1980) |
| 4,5'-dimethylangelicin | Vedaldi et al, Chem.-Biol. Interact, 36, 275 (1981) |
| psoralen | Marciani et al, Z. Naturforsch B, 27(2), 196 (1972) |
| 8-methoxypsoralen | Belognzov et al, Mutat. Res., 84, 11 (1981); Scott et al, Photochem. Photobiol., 34, 63 (1981) |
| 5-aminomethyl-8-methoxypsoralen | Hansen et al, Tet. Lett., 22, 1847 (1981) |
| 4,5,8-trimethyl-psoralen | Ben-Hur et al, Biochem. Biophys, Acta, 331, 181 (1973) |
| 4'-aminomethyl-4,5,8-trimethylpsoralen | Issacs et al, Biochem, 16, 1058 (1977) |
| xanthotoxin | Hradecma et al, Acta Virol., (Engl. Ed.) 26, 305 (1982) |
| khellin | Beaumont et al, Biochem. Biophys. Acta, 608, 1829 (1980) |
| R. Benzodipyrones | Murx et al, J. Het. Chem., 12, 417 (1975); Horter et al, Photochem. Photobiol., 20, 407 (1974) |
| S. Monstral Fast Blue | Jurarranz et al, Acta Histochem., 70, 130 (1982) |

Particularly useful intercalating agents are the azidointercalators. Their reactive nitrenes are readily generated at long wavelength ultraviolet or visible light and the nitrenes of arylazides prefer insertion reactions over their rearrangement products (White et al, *Methods in Enzymol.*, 47, 644 (1977)). Representative azidointercalators are 3-azidoacridine, 9-azidoacridine, ethidium monoazide, ethidium diazide, ethidium dimer azide (Mitchell et al, JACS, 104, 4265 (1982), 4-azido-7-chloroquinoline, and 2-azidofluorene. Other useful intercalators are the furocoumarins which form [2+2] cycloadducts with pyrimidine residues. Alkylating agents can also be used such as bis-chloroethylamines and expoxides or aziridines, e.g., aflatoxins, polycyclic hydrocarbon epoxides, mitomycin, and norphillin A.

Suitable angelicin derivatives for use in the present invention have the following formula

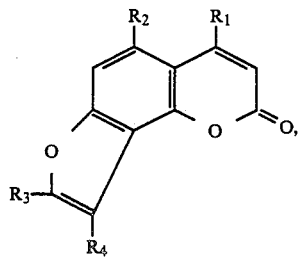

wherein $R_1$, $R_2$, $R_3$ and $R_4$ are as follows:

| $R_1$ | $R_2$ | $R_3$ | $R_4$ |
|---|---|---|---|
| H | H | H | H |
| $CH_3$ | H | $CH_3$ | H |
| $CH_3$ | $CH_3$ | $CH_3$ | $CH_2OH$ |
| $CH_3$ | H | $CH_3$ | $CH_2OCH_3$ |
| $CH_3$ | H | $CH_3$ | $CH_2NH_2$ |
| $CH_3$ | H | $CH_3$ | $CH_2Cl$ |
| $CH_3$ | H | $CH_3$ | 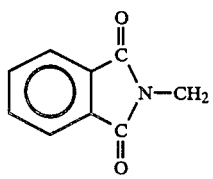 |

Many other compounds with different R's can be synthesized following published procedures.

Suitable psoralen perivatives for use in the present invention have the formula

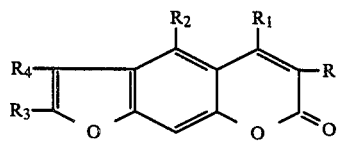

in which

R, $R_1$, and $R_3$ each independently is hydrogen or lower alkyl, $R_4$ is hydrogen, lower alkyl or lower alkyl substituted by hydroxy, lower alkoxy, amino, halo and/or

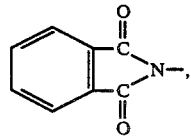

and $R_2$ and $R_5$ each independently is hydrogen, hydroxy, carboxy, carbo-lower alkoxy or lower alkoxy.

Angelicin derivatives are superior to psoralen compounds for monoadduct formation. If a single-stranded probe is covalently attached to some extra double-stranded DNA, use of phenanthridum and psoralen compounds is desirable since these compounds interact preferentially to double-stranded DNA in the dark.

Non-limiting examples of ligands for use in the present invention include haptens and biotin, e.g., biotin-N-hydroxysuccinimide and biotin-P-nitrophenyl ester.

Non-limiting examples of binding proteins for use in the present invention include antibodies, avidin and streptavidin.

Chemiluminescense precursors for use in the present invention include 2,3-dihydro-1,4-phthalazinediones ("DPD"). Preferably the 2,3-dihydro-1,4-phthalazinedione is of the formula

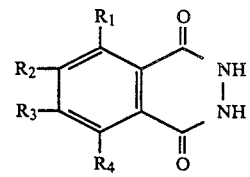

wherein $R_1$ is amino, and each of $R_2$, $R_3$ and $R_4$ is optionally substituted $C_1$-$C_6$-alkyl or alkenyl, hydroxyl, $C_1$-$C_6$-alkoxy, carboxyl or amino, or $R_2$ is amino and each of $R_1$, $R_3$ and $R_4$ is H, unsubstituted or substituted $C_1$-$C_6$-alkyl or alkenyl, hydroxyl, $C_1$-$C_6$-alkoxy, carboxyl or amino, or $R_1$ and $R_2$ are together and are an amino or substituted amino derivative of a benzo-group, and each of $R_3$ and $R_4$ is H, optionally substituted $C_1$-$C_6$-alkyl or alkenyl, hydroxyl, $C_1$-$C_6$-alkoxy, carboxyl, or amino. Particularly preferred chemiluminescence precursors are 5-amino-2,3-dihydro-1,4-phthalazinedione (luminol) and 6-amino-2,3-dihydro-1,4-phthalazinedione (isoluminol).

Substituted alkyl, alkenyl and amine radicals for use in the present invention are well known in the art. Non-limiting examples of substituents for such substituted radicals include halogen, e.g., chloro-, fluoro-, bromo- and iodo-, hydroxy, carboxy, nitro, cyano and thiol. Furthermore, amine radicals for use in the present invention can be substituted by alkyl, preferably having 1 to 10 carbon atoms, and alkenyl, preferably having 2 to 10 carbon atoms. Hydroxyl radicals for use in the present invention can be substituted by halogen, alkyl, preferably having 1 to 10 carbon atoms, or alkenyl, preferably having 2 to 10 carbon atoms.

Non-limiting examples of chemiluminescence enhancers include 4-chlorophenol, 4-bromophenol, 4-iodo phenol, 4-bromo-2-chlorophenol, 2,4-dichlorophenol, 3,4-di chlorophenol, 4-methylphenol, 4-tert. butylphenol, ethyl 3-(4-hydroxyphenyl)propionate, 4-benzylphenol, 4-(3'-methylcrotyl)phenol, 4-styrylphenol, 4-(2'4'-dinitrostyryl)phenol, 4-hydroxylcinnamic acid, alpha-cyano-4hydroxycinnamic acid, 4-phenylphenol, 4-(4'-hydroxyphenyl) phenol, 2-chloro-4-phenylphenol, 4-(4'-hydroxyphenyl)benzophenone, 4-(phenylazo)-phenol, 4-(2'-carboxylphenylazo) phenol, 4-phenoxyphenol, 4-(4'-hydroxyphenoxy)phenol, 4-hydroxyphenyl sulphide, 4-hydroxyphenyl disulphide, naphth-2-ol, 1-bromonaphth-2-ol, 6-bromomaphth-2-ol and 1,6-dibromonaphth-2-ol. A particularly preferred enhancer is 4iodophenol.

Other non-limiting examples of chemiluminescence enhancers for use in the present invention include 6-hydroxybenzothiazoles, such as 6-hydroxybenzothiazoles of the formula

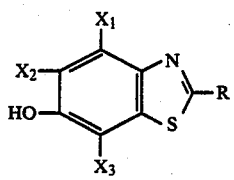

wherein R is H, CN or optionally substituted thiazole, and each of $X_1$, $X_2$ and $X_3$ is H, optionally substituted $C_1$-$C_6$-alkyl or alkenyl, hydroxyl, substituted hydroxyl, $C_1$-$C_6$-alkoxyl, carboxyl, amino or substituted amino. Particularly preferred chemiluminescence enhancers are firefly luciferin (4,5-dihydro-2-(6-hydroxy-2-benzothiazolyl)- thiazole-4-carboxoylic acid) and dehydroluciferin.

Generally any peroxidase enzyme can be used in the present invention. Non-limiting examples of enzymes for use in the present invention include horseradish peroxidase (HRP), microperoxidase and lactoperoxidase.

Any oxidant which reacts with the enzyme to cause excitation of the chemiluminescence precursor so that it emits light in a luminescent reaction, may be employed in the present invention. Particularly preferred oxidants are peroxides, e.g., hydrogen peroxide and sodium peroxide and perborate ion and peroxidate, for example, sodium peroxidate.

Light emission from the chemiluminescent reaction of the present invention, although depending primarily on the choice of enzyme, oxidant, enhancer and chemiluminescent precursor will also be determined by secondary factors such as temperature, pH, reagent concentration, mixing speed and method of light measurement. To maximize the sensitivity of the present system these secondary factors should be adjusted to obtain the maximum light emission, in a reproducible and easily messurable manner, with the signal to background ratio as high as possible.

The conditions chosen generally involve a compromise involving the catalytic activity of the enzyme, the type of oxidant employed, the kinetics of the reaction, the apparatus employed, the signal to background ratio and the sensitivity required.

In order to achieve optimum results the present chemiluminescent reactions should be conducted under moderate conditions of temperature ranging from 4° C. to 50° C., and pH, in the range of 6 to 10, preferably between 7 and 9. The process of the present invention is not limited to the above temperature ranges and temperature is not per se critical. Suitable buffering substances that can be employed in the present invention are phosphate, tris (hydroxmethyl) aminomethane, 2-amino-2-methyl-1,3-propanediol, acetate, carbonate and borate.

The following reagent concentrations (when added to a solution) are particularly suitable for use in the present invention:

enzyme: 0.01 ng to 5000 mg/liter
oxidant: 10 μmol to 300 mmol/liter
chemiluminescent precursor: 0.5 μmol to 200 mmol/liter
chemiluminescent enhancer: 1 μmol to 100 mmol/liter In a preferred embodiment of the present invention the probe is immobilized on a solid support, for example, nitrocellulose paper.

In one embodiment for carrying out the present invention, the labelled probe immobilized by hybridization on nitrocellulose paper, i.e., enclosed in a transparent container, is placed on high speed photographic film such as a "POLAROID" film cartridge. The immobilized probe and film cartridge, and suitable reagents in solution form (the reagents employed depend upon the probe utilized, for example, if the probe contains a chemiluminescence substance, then the reagent solution will contain an enhancer, an oxidant and an enzyme) would be injected into the vessel to contact the immobilized probe. Light emitted by virtue of a reaction between the reagents and the probe would then be detected on the film. It should be noted that the wavelength of light emitted would depend on the reagents employed. If hybridization occurs, light will be emitted. If hybridization does not occur, light will not be emitted.

Alternatively, emitted light can be detected by other means, such as by a photomultiplier tube, the signal from which can be fed to and displayed or recorded on a recorder, oscilliscope or scaler. The light could also be quantified on a luminometer.

Probes And Formats For Hybridization

There are different types of probes and formats which can be used for hybridization assays and detection by following the method of the present invention.

Essentially any nucleic acid hybridization format can be followed for the purposes of the present invention in which either the hybrids formed between the probe and the sequence to be determined or the probe which has not hybridized with the sequence of interest are labelable with the selected chemilumencescence label. As is known in the art, the labeling of such hybrids or unhybridized probe can be accomplished before or after the actual hybridization reaction. Normally, the probe is either labelled or labelable through a specific binding reattion or the formed hybrids are subsequently labeled, usually through a specific binding reaction. A central novel feature of the present invention is the advantageous application of the phenomenon of enhanced chemiluminescence to the detection of nucleic acid hybridization.

The probe will comprise at least one single stranded base sequence substantially complementary to or homologous with the sequence to be detected. However, such base sequence need not be a single continuous polynucleotide segment, but can be comprised of two or more individual segments interrupted by nonhomologous sequences. These nonhomologous sequences can be linear, or they can be self-complementary and form hairpin loops. In addition, the homologous region of the probe can be flanked at the 3'-5'-terminii by nonhomologous sequences, such as those comprising the DNA or RNA of a vector into which the homologous sequence had been inserted for propagation. In either instance, the probe as presented as an analytical reagent will exhibit detectable hbbridization at one or more points with sample nucleic acids of interest. Linear or circular single stranded polynucleotides can be used as the probe element, with major or minor portions being duplexed with a complementary polynucleotide strand or strands, provided that the critical homologous segment or segments are in single stranded form and available for hybridization with sample DNA or RNA. Particularly preferred will be linear or circular probes wherein the homologous probe sequence is in essentially only single stranded form (see particularly, Hu and Messing, *Gene*, 17, 271-277 (1982)).

The formats where a single polynucleotide sequence is used as a probe is common in the prior art. The probe can be labeled in such a way to enable its participation in the chemiluminescent reaction. This can be achieved by labeling the probe with a ligand as, for example, biotin which specifically binds to a protein and that protein can be a carrier for the chemiluminescent reaction component, as for example linked covalently to luminol or horseradish peroxidase or the chemiluminescent enhancer.

The probe can also be directly linked to the chemiluminescent reaction partners. The probe can be photochemically linked to luminol or the chemiluminescent enhancer or horseradish peroxidase. The probe can also be produced in such a fashion that after the hybridization the hybrid will behave immunologically distinct from the rest of the reaction components, for example, if a DNA probe is used for the detection of RNA or an RNA probe is used for the detection of DNA, the DNA/RNA hybrid produces immunologically specific antibodies which will recognize those hybrids and those specific recognition can be utilized for the detection of the hybrid. If the RNA probe is immobilized, the hybrid is likewise immobilized and an antibody specific for the RNA/DNA hybrid is reacted with the hybrid. If the antibody carries a label which can participate in the chemiluminescent reaction, the hybrid can be detected via the antibody and the chemiluminescent process. As, for example, if the RNA/DNA hybrid specific antibody is covalently linked to horseradish peroxidase after the hybridization and interaction with the peroxidase-linked antibody, it should be possible to initiate chemiluminescent reaction by adding the precursor, enhancer and an oxidant.

There are several other ways a nucleic acid can be made immunogenic and immunologically distinct from the other nucleic acids. Antibodies which are selective for RNA/RNA or DNA/DNA hybrids are also known and can be similarly used. In addition, if a nucleic acid interacts with an intercalator, the nucliic acid complex becomes immunologically distinct from the unreacted nucleic acid. In a hybridization format if a probe is prepared such that the probe will provide such interaction sites after the hybridization, an antibody assay can be conducted for the detection of the hybrid.

Practice of the analytical methods of the present invention is not limited to any particular hybridization format. Any conventional hybridization technique can be used. As improvements are made and as conceptually new formats are developed, such can be readily applied to carrying out the present method. Conventional hybridization forms which are particularly useful include those wherein the sample nucleotide acids or the polynucleotide probe is immobilized on a solid support (solid-phase hybridization) and those wherein the polynucleotide species are all in solution (solution hybridization).

Solid-Phase Hybridization Formats

In solid-phase hybridization formats, one of the polynucleotide species participating in hybridization is fixed in an appropriate manner in its single stranded form to a solid support. Useful solid supports are well known in the art and include those which bind nucleic acids either covalently or noncovalently. Noncovalent supports which are generally understood to involve hydrophobic bonding include naturally occurring and synthetic polymeric materials, such as nitrocellulose, derivatized nylon, and fluorinated polyhydrocarbons, in a variety of forms such as filters or solid sheets. Covalent binding supports are also useful and comprise materials having chemically reactive groups or groups, such as dichlorotriazine, diazobenzyloxymethyl, and the like, which can be activated for binding to polynucleotides.

A typical solid-phase hybridization technique begins with immobilization of sample nucleic acids onto the support in single stranded form. This initial step essentially prevents reannealing of complementary strands from the sample and can be used as a means for concentrating sample material on the support for enhanced detectability. The polynucleotide probe is then contacted with the support and hybridization detected by the methods as described herein.

Normally, the probe is labeled directly or indirectly through one or more specific binding pairs with the selected chemiluminescence label. As used herein, indirect labeling, immobilization, or other modification through one or more specific binding pairs intends the coupling of one of a pair of mutually binding substances to the material to be labeled, etc., e.g., probe, and the labeling, immobilization, etc. of the other member of the pair. Useful binding pairs include biotin/avidin (including egg white avidin and streptavidin), haptens and antigens/antibodies, carbohydrates/lectins, enzymes-/inhibitors, and the like as are known in the art. One can also use bridging pairs, such as coupling biotin or a hapten to the material to be labeled, etc., and also to the label, solid-phase, etc., and using avidin or an antihapten, respectively, to bridge the two.

When using labeled probe and immobilized sample nucleic acids, the resulting hybrids are separated from the unhybridized probe, and the chemiluminescence reaction is initiated in one or the other of the separate fractions. Alternatively, the hybrids and unhybridized probe do not have to be separated if hybrids are detected by anti-hybrid antibodies which distinguish the hybrids from the unhybridized single stranded probe. Such antibodies can be selective for mixed DNA/RNA hybrids or selective on RNA/RNA or DNA/DNA hybrids, or can be selective for intercalator duplexes where an intercalating agent has been introduced to the hybrids. Such antibody reagents will be describe in more detail below.

An alternative method to those involving sample nucleic acid immobilization uses immobilized probe and detection of resulting immobilized hybrids with an anti-hybrid antibody labeled directly or through specific binding pairs with the selected chemiluminescence label as described above. When presented to the hybridization reaction in an immobilized form, the probe can be in any appropriate form that enables the probe, and any components of the reaction mixture that have become associated therewith by hybridization and/or by binding of the antihybrid reagent, to be subsequently isolated or separated from the remaining mixture such as by centrifugation, filtration, chromatography, or decanting. A variety of compositions and configurations of an immobilized probe will thus be evident and available to the worker in the field Essentially any form of the probe that is insoluble in the reaction mixture can be used For example, the probe can be aggregated or otherwise precipitated, attached to an insoluble material, polymer, or support, or entrapped in a gel such as agarose or polyacrylamide (see *Meth. Enzymol.*, 12B:635 (1968) and PNAS, 67, 807 (1970)). It is particularly preferred to employ a solid support to which the probe is attached or fixed by covalent or noncovalent bonds, the latter including adsorption methods that provide for a suitably stable and strong attachment. The solid support can take on a variety of shapes and compositions, including microparticles, beads, porous and impermeable strips and membranes, the interior surface of reaction vessels such as test tubes and microtiter plates, and the like. Means for attaching a desired reaction partner to a selected solid support will be a matter of routine skill to the worker in the field.

One method for adsorbing the probe onto nitrocellulose membranes involves saturating a solution of probe with sodium iodide and spotting or filtering aliquots onto the membrane (Bresser et al, *DNA*, 2, 243 (1983)). The sodium iodide facilitates denaturation of the probe and enhances adsorption onto the membrane. Alternatively, the probe can be treated with glyoxal, usually at concentrations around 1 molar(M), and then adsorbed onto the membrane. The probe is fixed by baking at around 80° C. under vacuum for a period in the range of 2–4 hours. (P. S. Thomas, *Meth. In. Enzymol.*, 100, 255 (1983)).

Covalent immobilization of RNA or DNA probes can also be accomplished. A wide variety of support materials and coupling techniques can be employed. For example, the probe can be coupled to phosphocellulose through phosphate groups activated by carbodiimide or carbonyldiimidazole (E. K. F. Bautz, and B. D. Hall, *Proc. Nat'. Acad. Sci. USA*, 48, 400–408 (1962); T. Y. Shih and M. A. Martin, *Biochem*, 13, 3411–3418 (1974). Also, diazo groups on m-diazobenzoyloxymethyl cellulose can react with guanine and thymidine residues of the polynucleotide (B. E. Noyes and G. R. Stark, *Cell*, 5, 301–310 (1975); J. Reiser et al, *Biochem. Biophys. Res. Commun.*, 85, 1104–1112 (1978)). Polysaccharide supports can also be used with coupling through phosphodiester links formed between the terminal phosphate of the polynucleotide and the support hydroxyls by water soluble carbodiimide activation (D. Richard, *Biochim. Biophys. Acta*, 269, 47–50 (1972); P. T. Gilham, Biochem, 7, 2809–2813 (1968)), or by coupling nucleophilic sites on the polynucleotide with a cyanogen bromide activated support (D. J. Arndt-Jovin et al, *Eur. J. Biochem.*, 54, 411–418 (1975); U. Linberg and S. Ericksson, *Eur. J. Biochem.*, 18, 474–479 (1971)). Further, the 3'-hydroxyl terminus of the probe can be oxidized by periodate and coupled by Schiff base formation with supports bearing amine or hydrazide groups (P. T. Gilham, *Method. Enzymol.*, 21, 191–197 (1971); H. D. Hansske et al, *Method. Enzymol.*, 59, 172–181 (1979)). Supports having nucleophilic sites can be reacted with cyanuric chloride and then with the polynucleotide (H. D. Hunger et al, *Biochim Biophys. Acta*, 653, 344–349 (1981)).

In general, any method can be employed for immobilizing the probe provided that the complementary single stranded sequence is available for hybridization to sample nucleic acids. Particular methods or materials are not critical to the present invention.

Another method of interest is the sandwich hybridization technique wherein one of two mutually exclusive fragments of the homologous sequence of the probe is immobilized and the other is labeled. The presence of the poyynucleotide of interest results in dual hybridization to the immobilized and labeled probe segments, again with the same ultimate measurement of support-associated labeled hybrids. See *Methods in Enzymology*, 65, 468 (1980) and Gene, 21, 77–85 (1983) for further details.

For purposes of better illustration, the following solid-phase hybridization methods involving detection with antibody to intercalated duplexes are particularly useful in the present invention.

In a first method, the siggle stranded nucleic acids from the liquid test medium are first immobilized on a solid support. A hybridization reaction mixture is then formed by contacting the immobilized sample nucleic acids with the probe which in this case comprises, in addition to the complementary single stranded portion, at least one double stranded portion which is chemically linked with the intercalator in the form of intercalation complexes. A particularly useful form of the probe is the circular form described by Hu and Messing, supra. The resulting hybridization aggregate comprises the immobilized polynucleotide of interest hybridized with the probe which has a covalently linked, intercalated double stranded region. The solid support carrying immobilized duplexes is then preferentially separated from the remainder of the reaction mixture. The antibody is added, preferably labeled with the selected chemiluminescence label, and the resulting immobilized antibody bound to intercalation complexes in the aggregate is separated from the remainder of the reaction mixture. The antibody bound to the support is then determined to complete the assay. Alternatively, the antibody in the separated solution can be determined; although this will generally be less preferred since a large excess of antibody is normally used.

A variation of this method is to employ a probe such as above, but not having covalently linked intercalator bound to the double stranded region. Rather, the intercalator is added to the immobilized aggregate resulting in the formation of intercalator complexes in both the double stranded portion of the probe and the duplexed region formed by hybridization.

A second method is based on a sandwich format where a reaction mixture is formed among the test medium containing the sequence of interest and the first and second probes, each comprising respectively at least one base sequence complementary to a mutually exclusive portion of the sequence of interest. The first probe is immobilized on a solid support and the second probe is modified with covalently linked, intercalation complexes as in the previous methods. The resulting hybridization aggregate comprises the sequence of interest hybridized to both the immobilized first probe and the intercalation complex-modified second probe. The antibody is added, preferably in labeled form, and the resulting immobilized antibody bound to intercalation complexes in the aggregate is separated from the remainder of the reaction mixture. The bound antibody is determined to then complete the assay.

There are several useful variations of this second method. First, as in the case of the variation of the first method, one can employ a probe which does not comprise covalently linked intercalator, but rather can add free intercalator to the immobilized aggregate, resulting in the formation of intercalator complexes with all available double stranded regions. Also, as an alternative to using a second probe with a double stranded portion, one can use a probe of entirely single stranded nucleic acid with intercalator chemically linked thereto so that upon hybridization there are formed intercalation complexes, or with intercalator being added so that intercalation occurs between the duplexes formed between the two probes and the sequence to be detected.

In a third method, the sample nucleic acids are contacted with immobilized probe and preferably the resulting immobilized duplexes are separated from the remainder of the reaction mixture. In this format, the probe is in single stranded form. The resulting hybridization product comprises the immobilized probe hybridized with the sequence of interest. Also, this format allows significant reannealing between complementary regions of sample nucleic acid which can take place on the immobilized aggregate. Such reannealing works to the advantage of the assay since it provides additional double stranded nucleic acid for subsequent intercalation. The next step in the assay is to add intercalator and the antibody, again preferably in a labeled form. The assay is completed by separation and antibody determination steps as in the previous formats.

Finally, there is a fourth method wherein the single stranded sample nucleic acids are contacted with immobilized probe where, in this case, such probe is chemically, e.g., covalently linked to the intercalator such that duplex formation in the region of the linked intercalator results in formation of intercalation complexes. This is a highly advantageous format in that the probe is both immobilized and modified, requiring no immobilization or modification step to be performed at the time of the assay. The resulting aggregate comprises covalently linked, intercalation complexes in the region of hybridization between sample and probe nucleic acids and in any reannealed sample regions. Antibody is then added and the assay completed as in the previous formats. This format provides the advantage of eliminating the need for the analyst to handle solutions of the free intercalator which in some cases can be potentially hazardous. A simple variation of this technique is to immobilize sample nucleic acids rather than the labeled probe and proceed in the normal fashion. This is somewhat less advantageous but is a practical assay approach.

Solution-Phase Hybridization Formats

In addition to the above described solid-phase formats, a variety of solution-phase hybridization formats can also be applied to the present invention. Such formats are characterized by the feature that the hybridization step involves soluble forms of both the sample nucleic acids and the probe. This can result in significantly faster hybridizations since the kinetics are much faster when both strands are in solution compared to when on is immobilized. Normally, subsequent to the hybridization step, the resulting hybrids are rendered immobile for purposes of detection. Such immobilization can be accomplished in a variety of ways. Conventionally it is known to selectively immobilize complexes by exposure to adsorbents such as hydroxyapatite and nitrocellulose membranes.

A particularly useful approach to immobilizing hybrids formed from a solution-phase hybridization involves the use of a probe which comprises a reactive site capable of forming a stable covalent or noncovalent bond with a reaction partner and obtaining immobilization by exposure to an immobilized form of such reaction partner. Preferably, such reactive site in the probe is a binding site such as a biotin or hapten moiety which is capable of specific noncovalent binding with a binding substance such as avidin or an antibody which serves as the reaction partner. After the hybridization step then, one can add an immobilized form of the reaction partner, e.g., binding substance, which will effectively bind and immobilize the hybrids through the reactive site on the probe.

Essentially any pair of substances can comprise the reactive site/reactive partner pair which exhibit an appropriate affinity for interacting to form a stable bond, that is a linking or coupling between the two which remains substantially intact during the subsequent assay steps, principally the separation and detection steps. The bond formed may be a covalent bond or a noncovalent interaction, the latter being preferred especially when characterized by a degree of selectivity or specificity. In the case of such preferred bond formation, the reactive site on the probe will be referred to as a binding site and the reaction partner as a binding substance with which it forms a noncovalent, commonly specific, bond or linkage. Such binding site can be present in a single stranded hybridizable portion of the probe or can be present as a result of a chemical modification of the probe. Examples of binding sites existing in the nucleotide sequence are where the probe comprises a promoter sequence (e.g., lac-promoter, trp-promoter) which is bindable by a promoter protein (e.g., bacteriophage promoters, RNA polymerase), or comprises an operator sequence (e.g., lac operator) which is bindable by a repressor protein (e.g., lac repressor), or comrrises rare, antigenic nucleotides or sequences (e.g., 5-bromo or 5-iododeoxyuridine, Z-DNA) which are bindable by specific antibodies (see British Patent Specification No. 2,125,964). Binding sites introduced by chemical modification of the probe are particularly useful and normally involve linking one member of a specific binding pair to the probe nucleic acid. Useful binding pairs from which to choose include biotin/avidin, haptens and antigens/antibodies, carbohydrates/lectins, enzymes/inhibitors, and the like. Where the binding pair consists of a proteinaceous member and a nonproteinaceous member, it will be preferred to link the nonproteinaceous member to the probe since the proteinaceous member may be unstable under the denaturing conditions of hybridization of the probe. Preferable systems involve linking the probe with biotin or a hapten and employing immobilized avidin or anti-hapten antibody, respectively. Preparation of useful ligand-labeled probes is known in the literature (Langer et al, *Proc. Natl. Acad. Sci.*, 78, 6633 (1981); Broker, (1978), *Nucl. Acids Res.*, 5, 363; Sodja et al, *Nucl. Acids Res.*, 5, 385 (1978); Tchen et al, *Proc. Natl. Acad. Sci.*, 81, 3466 (1984)). Immobilization of the binding substance can follow conventional techniques.

A large variety of methods are known for immobilizing proteins on solid supports and these methods are applicable to the immobilization of the binding substance (see *Methods in Enzymology*, Vol. 44 (1976)). Antibodies, for example, are immobilized either by covalent coupling or by noncovalent adsorption. Noncovalent methods frequently employed are adsorption to polystyrene beads or microparticles and to polyvinylchloride surface. Many covalent methods are used for immobilizing proteins and a few include cyanogen bromide activated agaroses and dextrans; glutaraldehyde activated nylons and polyacrylamides; and epoxides on acrylic and other supports.

When the probe is presented for hybridization with the sequence of interest in an immobilizable form, the subsequent steps of immobilization of the formed duplexes through a property of the probe and addition of the anti-hybrid reagent can proceed in any desired order. Immobilization and anti-hybrid addition can be accomplished by simultaneous addition of the involved reagents and materials, or one can precede the other, with or without intervening wash or separation steps, in either order. Where ordered additions are followed, of course one will take into account the concentrations of the added reagents so as not to oversaturate the formed hybrids and inhibit interaction therewith of the second added materials. Although immobilized probes or immobilizable probes which become bound to solid supports by specific binding processes described above are preferred, immobilizable probes can be bound to supports by processes with relatively low specificity. In this case the support would bind the hybridized probe but not the unhybridized form. Then the mmount of hybrid would be measured with the antibody reagent. An example of a support of this type is hydroxyapitite which binds DNA·RNA and RNA·RNA duplexes but not the single stranded species (Brenner and Falkow, *Adv. in Genet.*, 16, 81 (1973)).

Also, a chemically active or activatable group can be introduced into the probe and allowed to react with the solid support following the hybridization. This system would give a convalently immobilized probe and the amount of hybrid coupled to the support can be determined with the antibody.

In addition to the above methods, solution-phase hybridization formats can be performed wherein the hybrids are immobilized by binding of immobilized or immobilizable anti-hybrid antibody reagents. Such antibody reagents can be specific for intercolated dulexes or for DNA/RNA, RNA/RNA, or DNA/DNA hybrids as described herein. Resulting immobilized duplexes are detected by using directly or indirectly labeled probe, labeled second anti-hybrid antibody, or a labeled second probe.

Anti-Hybrid Antibody Reagent and Detection Schemes

The antibody reagent used in the preferred embodiments of the present invention is principally characterized by its ability to bind the hybrids formed between the probe and complementary sample nucleic acids to the significant exclusion of single stranded polynucleotides. The antibody reagent can consist of whole antibodies, antibody fragments, polyfunctional antibody aggregates, or in general any substance comprising one or more specific binding sites from an anti-hybrid antibody. When in the form of whole antibody, it can belong to any of the classes and subclasses of known immunoglobulins, e.g., IgG, IgM, and so forth. Any fragment of any such antibody which retains specific binding affinity for the hybridized probe can also be employed, for instance, the fragments of IgG conventionally known as Fab, F(ab'), and F(ab')$_2$. In addition, aggregates, polymers, derivatives and conjugates of immunoglobulins or their fragments can be used where appropriate.

The immunoglobulin source for the antibody reagent can be obtained in any available manner such as conventional antiserum and monoclonal techniques. Antiserum can be obtained by well-established techniques involving immunization of an animal, such as a mouse, rabbit, guinea pig or goat, with an appropriate immunogen. The immunoglobulins can also be obtained by somatic cell hybridization techniques, such resulting in what are commonly referred to as monoclonal antibodies, also involving the use of an appropriate immunogen.

Useful anti-hybrid antibodies include those selective for intercalated nucleic acid duplexes as well as those which bind DNA/RNA, RNA/RNA, or DNA/DNA hybrids specifically.

Antibodies to intercalated duplexes are raised against an immunogen which usually comprises an ionic complex between catonic protein or protein derivative (e.g., methylated bovine serum albumin) and the anionic intercalated duplexes. Preferably, the intercalated is covalently linked to the duplex. Alternatively, the intercalator-duplex complex can be covalently coupled to a carrier protein.

The preparation of antibodies to DNA/DNA is described in European Patent Publication No 135,139.

Immunogens for stimulating antibodies specific for DNA/RNA hybrids can comprise homopolymeric or heteropolymeric polynucleotide duplexes. Among the possible homopolymer duplexes particularly preferred is poly(rA)·poly(dT) (Kitagawa and Stollar, *Mol. Immunol.*, 19, 413 (1982)). However, in general, heteropolymer duplexes will be preferably used and can be prepared in a variety of ways, including transcription of $\phi$X174 virion DNA with RNA polymerase (Nakazato, *Biochem*, 19, 2835 (1980)). The selected RNA DNA duplexes are adsorbed to a methylated protein, or otherwise linked to a conventional immunogenic carrier material, such as bovine serum albumin, and injected into the desired host animal (see Stollar, *Meth. Enzymol.*, 70, 70 (1980)).

Antibodies to RNADNA duplexes can be raised against double stranded RNAs from viruses such as reovirus or Fiji disease virus which infects sugar cane, among others. Also, homopolymer duplexes such as poly(rI)·poly(rC) or poly(rA)·poly(rU), among others, can be used for immunization as above.

When the antibody reagent is used to detect hybrids, it will usually be labeled with the chemiluminescence label by suitable synthetic means. Alternatively, the antibody reagent can be detected based on a native property such as its own antigenicity. A chemiluminescence labeled anti-(antibody) antibody or protein A will bind to the primary antibody reagent where the label for the second antibody or protein A as above. Further, antibody can be detected by complement fixation or the use of labeled protein A, as well as other techniques known in the art for detecting antibodies.

Where the antibody reagent is labeled, as is preferred, the labeling moiety and the antibody reagent are associated or linked to one another by direct chemical linkage such as involving covalent bonds, or by indirect linkage such as by incorporation of the label in a microcapsule or liposome which is in turn linked to the antibody. Labeling techniques are well-known in the art and any convenient method can be used in the present invention.

The invention will now be described with reference to the following non-limiting examples.

EXAMPLES

EXAMPLE 1

The effect of DNA and DNA modifying agents on the chemiluminescent reaction delayed by luciferin FIG. 1 shows the effect of DNA on light emission rate measured in a SLM 4800 Spectroflurometer. Experiments were carried out by adding 200 microliters(mcl) of 0.2 mM luminol plus 5 mM hydrogen peroxide in 1:1 mixture to a solution containing 100 mcl of nucleic acid. The total amount of nucleic acid present in the mixture was respectively 1 $\mu$g, 5 $\mu$g and 10 $\mu$g. The horseradish peroxidase concentration was 100 per ml. The specific activity was 250 units per mg purchased from Sigma Chemical Co., St. Louis, Miss., U.S.A. The horseradish peroxidase was biotinylated so that when the nucleic acid hybridization was studied the same enzyme was used. The total final volume of the reaction mixture was adjusted to 2.4 ml by adding 10 millimolar tris buffer (pH of 8.1). FIG. 1 clearly indicates that the nucleic acid has virtually no effect on the process. FIG. 2 and FIG. 3 show that under identical conditions biotinylated DNA might have some irradiating effect on emission. The photochemically biotinylated nucleic acid which had been biotinylated by reacting DNA with biotin angelicin adduct and irradiated at 346 Nm did not show the kind of effect which is shown by nick-translated commercially available products. The effect of the nick-translated nucleic acid is not clearly understood, but at this point if photochemical biotinylation method is conducted the effect of the nucleic acid on the chemiluminescent reactions can further be reduced by using avadin. FIG. 4, FIG. 5 and FIG. 6 show the results of the effect of angelicin, biotin and luciferin, respectively. In order to utilize the horseradish peroxidase mediated process for the detection of nucleic acid hybrids, four different types of formats were utilized so that ultimately horseradish peroxidase of a similar enzyme assay could be used to monitor the final reaction results.

EXAMPLE 2

PREPARATION OF LIGAND-BOUND PROBE DNA

Although the method below is illustrated with a specific nucleic acid probe, it can be used for any DNA probe. Various other methods of labeling (nick translation, for example) nucleic acid probes are known in the literature. The method is general for nucleic acids, hence a test sample can also be labeled by this method. The principle of the method is described below

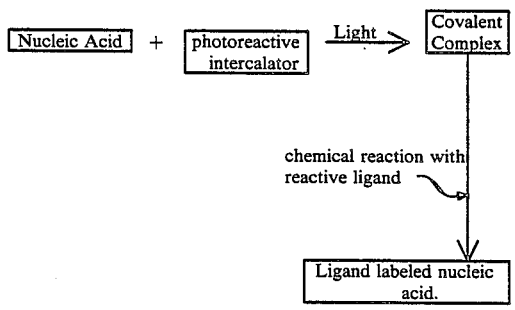

In the above, the following were employed:
(a) an ADENOVIRUS DNA or pBR322 probe (commercially available plasmid DNA probe from ENZO Bio Chem, New York, U.S.A. and BRL - Bethesda Research Laboratory, Maryland, U.S.A.).
(b) the photoreactive intercalator was an aminomethyl angelicin,
(c) the reactive ligand was N-hydroxysuccinimido biotin.

The probe was first photochemically reacted with an intercalator. The intercalator was then reacted with a reactive residue of biotin. The order can be changed so that biotin residues are reacted first with a photoreactive intercalator, then the product can be photochemcally reacted with the probe.

A 50 μg DNA probe was dissolved in 0.500 ml borate buffer (10 mn pH 8.2) and to the solution 5 μl (5 μg) aminomethyl angelicin (1 mg/ml in $H_2O$) was added. The solution was irradiated at 346 nm for 30 minutes. The reacted nucleic acid was purified by precipitation with ethanol. The $-NH_2$ residue of the bound angelicin was reactive and could be modified with N-hydroxysuccinimide derivative of biotin (NHS biotin) This was done by dissolving aminomethyl-angelicin coupled nucleic acids (lmg/ml) in borate buffer (10 mM pH 8.2) and adding 10 times molar excess of NHS biotin (dissolved in DMF 10 mg/ml). The mixture was shaken for 8 hours at room temperature. The resulting biotinylated DNA was purified by dialysis against phosphate buffer (10 mM $NaH_2PO_4$, 10 mM $Na_2HPO_4$, 1 mM EDTA pH 7.5). The resulting biotinylated probe was ready for hybridization.

EXAMPLE 3

DOT-BLOT ASSAY FOR DNA 100 ng to 1 pg photochemically biotinylated DNA were spotted on BioRad nitrocellulose paper, baked in an oven at 80° C. for two hours; saturated with BSA (bovine serum albumin) by immersing the paper in 3% BSA at 42° C. for 20 minute. Excess BSA was removed by taking the paper out of the container and blotting it between two pieces of filler papers. The paper was then incubated in a solution containing Streptavidin (0.25 mg/ml, 3.0 ml total volume), for 20 minutes at room temperature. It was then washed three times with a buffer containing Tris 0.1M, pH 7.5 0.1M NaCl, 2 mm $MgCl_2$ and 0.05% Triton X. It was incubated with biotinylated horseradish peroxidase (0.1 mg/ml) for 15 minutes at room temperature. This was followed by three washings with Tris (0.1M, pH 7.5), 0.1M NaCl, 2 mM $MgCl_2$ and 0.05% Triton X-100. Spots were punched out and the discs containing the DNA were placed in microtiter plate wells which were painted black on the sides. After the punched paper circles were placed in the microtiter plate wells, 0.8 ml buffer containing 40 mM tris and 40 mM ammoninum acetate (pH 8.1) was added to each well. Then 10 μl of 1:1 (v/v) mixture of 39 mM luminol in DMF and 30mM $H_2O_2$ in water was added and a photograph of emitted light was taken. After the light decayed more, a $H_2O_2$+luminol mixture was added. The reaction was continued for three days with approximately loss of enzyme activity.

EXAMPLE 4

Hybridization of Biotinylated Probe and Detection by Chemiluminescent Reaction

Solutions:
A. Tris-HCL buffer (1M; pH 7.5)
B. 0.5M NaOH solution
C. Tris-HCl (0.5M; pH 7.5)
D. 3 Molar NaCl
E. SSC X 20: 175 g NaCl
   88 g Na-Citrate
   water to make 1 liter
   pH adjusted to 7.0 with HCl
   This was diluted with water to produce different SSC concentrations
F. Prehybridization Solution:
   45% formamide
   50mm Na-phosphate buffer pH 6.5

5xSSC
5x Denhardts solution
200 μg/ml single-stranded DNA in water

G. Hybridization Solution:
45% formamide
20 mm Na-phosphate buffer pH 6.5
5 xSSC
5 x Denhardts solution
100 μg/ml single-stranded DNA in water Method:

1 μg to 1 pg of test sample DNA and control DNA (should not hybridize with the probe) were spotted onto nitrocellulose paper. The DNA samples were denatured by contacting the paper with a 3MM Whatman cellulose paper (which was soaked in and saturated with 0.5M NaOH) for 7 minutes. Then the nitrocellulose paper was brought in contact with another wet 3MM paper (which was soaked in Solution A for neutralization). The paper was dried after 2 minutes. The neutralization and drying under vacuum was repeated three times.

The nitrocellulose paper containing the immobilized denatured DNA was then contacted with a 3MM paper soaked in and saturated with solutions C and D for 5 minutes. The paper was then baked at 80° C. under vacuum for two hours. The filter was then placed in a plastic bag containing 10 mls of Solution F. The bag was incubated at 42° C. for two hours in a water bath. After prehybridization, the paper was taken out and placed in another bag containing 10 mls of solution G and lug labeled denatured probe (product of Example 1). Hybridization was conducted at 42° C. for 16 hours.

The nitrocellulose paper was then washed sequentially as follows:

a. with 250 ml 1xSSC+0.1% SDS: 2 washes, 3 minutes at room temperature.
b. with 250 ml 0.2 SSC+0.1% SDS: 2 washes, 3 minutes at room temperature.
c. with 250 ml 0.16xSSC+0.1% SDS: 2 washes, 15 minutes at 50° C.
d. with 50 ml 2 xSSC+0.1% SDS: 1 wash, 1 minute at room temperature.

The hybrids were then detected by chemiluminescent reaction as follows : The filters with the hybrids were saturated with BSA (bovine serum albumin) by immersing the paper in 3% BSA at 42° C. for 20 minutes. Excess BSA was removed by taking the paper out of the container, and blotting it between two pieces of filter paper. The paper was then incubated in a solution containing Streptavidin (0.25 mg/ml, 3.0ml total volume), for 20 minutes at room temperature. It was then washed three times with a buffer containing Tris 0.1M, pH 7.5 0.1M NaCl, 2 mm $MgCl_2$ and 0.05% Triton X. Next the filter was incubated with biotinylated horseradish peroxidase (0.10 mg/ml) for 15 minutes at room temperature. This was followed by three washings with Tris (0.1M, pH 7.5), 0.1M NaCl, 2 mM $MgCl_2$ and 0.05% Triton X-100 and one washing with 10 mM Tris (pH 8.0) buffer. Spots were punched out and the discs containing the DNA were placed in a microtiter plate with wells which were painted black on the sides. After the punched paper circles were placed in the microtiter plate wells, 0.8 ml buffer containing 40 mM Tris and 40 mM ammonium acetate (pH 8.1) was added to each well. Then 10 μl of a 1:1 mixture of 39 mM Luminol (in DMF) and 30 mM $H_2O_2$ (in water) was added. Light emission was recorded on a "POLAROID" instant film by exposing it directly in the film holder.

Alternatively, in a dark room the light emitting papers were wrapped with transparent plastic paper, e.g., "SARAÑ WRAP", and put directly on the open film (cover pulled using a film holder). After they were exposed the cover was replaced and the film was developed and processed by pulling it out.

EXAMPLE 5

Preparation of Enzyme-Labeled Probe and Chemiluminescent Detection of Nucleic Acid Hybrid As has been described by Renz et al (*Nucleic Acids Res.*, 12, 3435 (1984)) a nucleic acid probe is chemically linked to horseradish peroxidase and hybridized to the immobilized test sample (Example 4). The method and conditions of hybridization are identical to the published precedure (*Nucleic Acids Res.*, 12, 3435 (1984)). After the hybridization the paper is washed with Tris buffer (10 mM, pH 0.8), spots are punched out and detected as described in Example 4. No post-hybridization BSA blocking is necessary when an enzyme-labeled probe is used.

EXAMPLE 6
PREPARATION OF PHOTOREACTIVE ISOLUMINOL DERIVATIVE AND HYBRIDIZATION
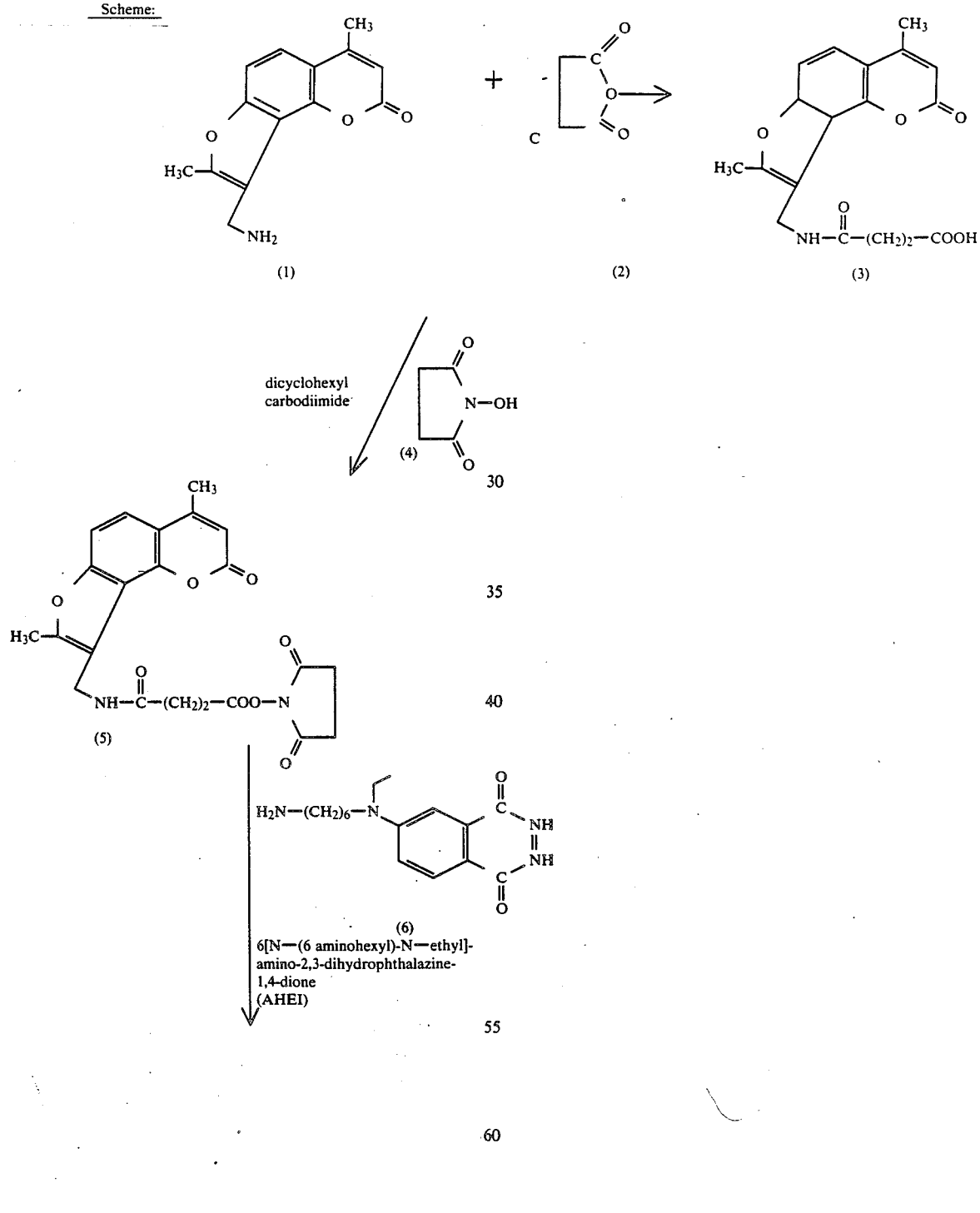

Scheme:

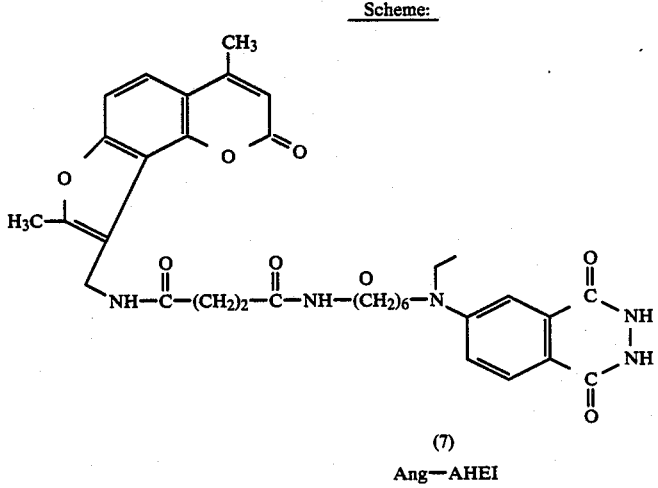

(7)
Ang—AHEI 100 mg of 4'aminomethyl-4,5'-dimethylangelicin (1) and 0.4 gm of succinic anhydride is shaken together in anhydrous pyridine (5 ml) for 24 hours. Pyridine is evaporated, the residue is treated with methanol; the solvent is evaporated to a gummy mass. The solid is placed in 10 ml DMF and 0.2 gm of dicyclohexyl carbodiimide and 0.4 gm of N-hydroxysuccinimide are added. The reaction is carried out for 24 hours. The rection mixture is cooled to $-20°$ C. to precipitate dicyclohexylurea, which is removed by centrifugation. The resulting product is reacted with 3 times molar excess of AHEI (6) in DMF. The reaction is conducted by incubating the mixture for 12 hours at room temperature. DMF is then evaporated under reduced pressure. The resulting solid can be used without purification. The solid is dissolved in 10 ml DMF and 1.0 μl of this solution is added to 1 ml probe (50 μg) to be labeled and photoirradiation is conducted as in Example 2, then hybridized as in Example 4.

After hybridization, the spots are placed separately in microtiter plate wells. 1 μl (0.1 mg/ml) horseradish peroxidase, 1 ml Tris-ammonium buffer (40 mM Tris+40 mM ammonium) and 0.5 ml, 5 mM $H_2O_2$ are added. Light emission is recorded by exposing "PO-LAROID" film.

EXAMPLE 7
COUPLING OF ENHANCER TO A DNA PROBE

Firefly D-luciferin or

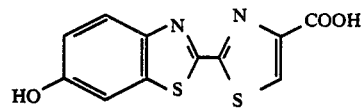

is activated with N-hydroxysuccinimide as in Example 6 and then is reacted with 4'-aminomethyl-4,5'-dimethylangelicin reacted probe as in Example 2. Hybridization is conducted in an identical method as described in Example 4. The detection requires the addition of 1 μl (0.1 mg/ml) horseradish peroxidase, 0.1 ml 1:1 mixture of 0.5 mM luminol (in DMF) and 5 mM $H_2O_2$. This method reduces the background emission, since delayed enhanced chemiluminescence is accomplished only from the hybridized probe.

EXAMPLE 8
OLIGONUCLEOTIDE DETECTION AFTER HYBRIDIZATION

This example was divided into four parts, namely:
8a. Synthesis of an amine containing oligonucleotide;
8b. Reaction of 8a product with N-hydroxysuccinimido biotin;
8c. Purification of 8b product; and
8d. Hybridization and detection of oligonucleotide by chemiluminescence.

EXAMPLE 8a
SYNTHESIS OF A REACTIVE AMINE-CONTAINING OLIGONUCLEOTIDE

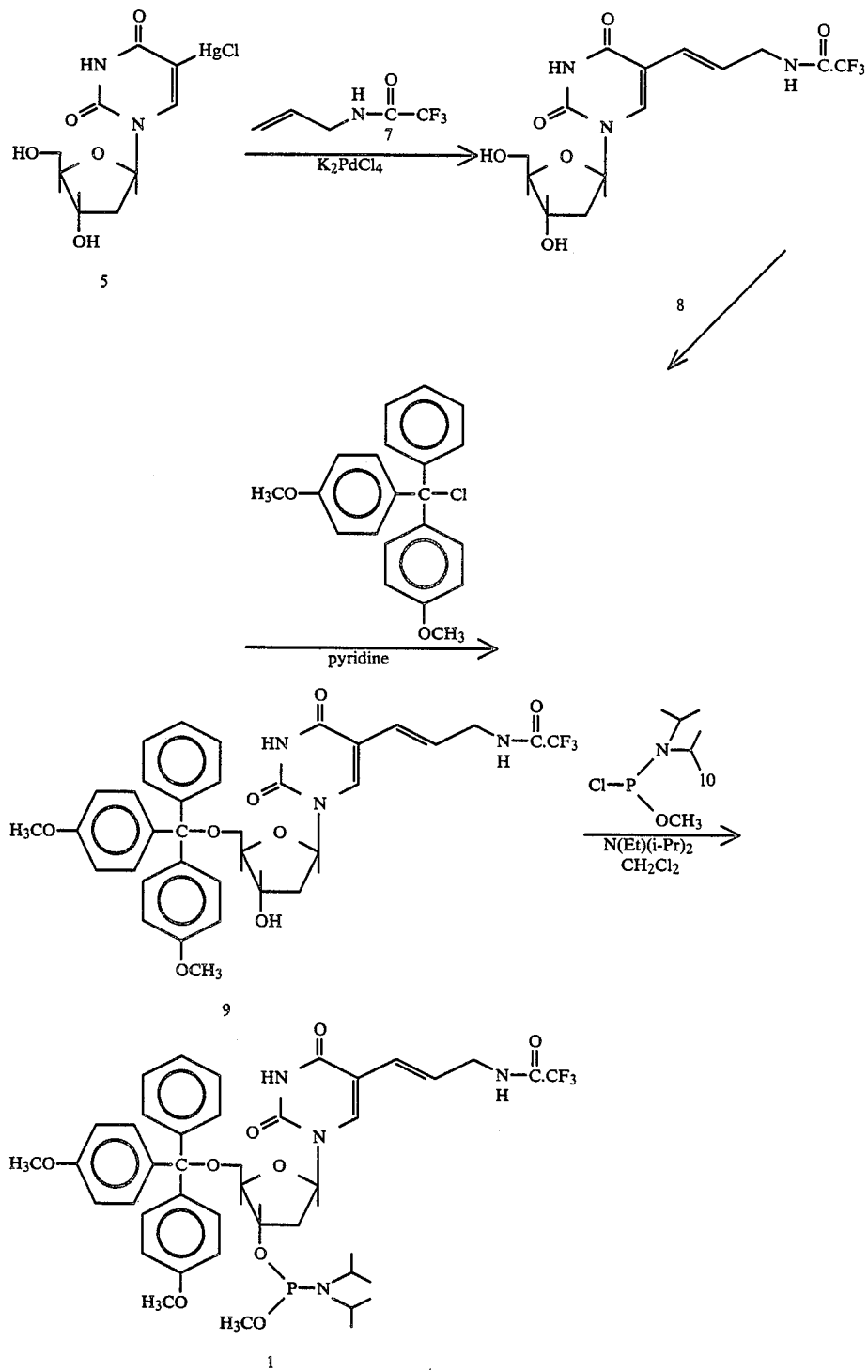

pene (7) (M. Paileand, W. J. Hubsch, *Monatshefte fur Chemie*, 97, 99 (1966)) and $K_2PdCl_4$ in methanol to give 5-trifluoroacetamidoallyl-2'deoxyuridine (8) in 22% yield after two chromatographies and a crystallization Scheme for the synthesis of 1 to be added to 19A' at the 5' end.

The synthesis of 1 is outlined in the above scheme
5-Chloromercuri-2'-deoxyuridine (5), prepared according to the method of D. E. Berstrom and J. L. Ruth, *J. Carbohydrates, Nucleosides, and Nucleotides*, 4, 257 (1977), was treated with 3-trifluroacetamido-1-profrom methanol. Reaction of 8 with 4,4'-dimethoxytrityl chloride in pyridine produced 9 in 85% yield after flash chromatograph (W. C. Still, M. Kahn, A. Mitra, *J. Org. Chem.*, 43, 2923 (1978), which was subsequently treated with N,N-diisopropylaminomethoxy chlorophosphine (L. J. McBride and M. H. Caruthers, *Tet. Letters*, 24, 245 (1983)) (10) to give 1 as a white solid after precipitation from pentane. 19-unit oligonucleotides HBl9A':

3'-GA-GGA-CXC-CTC-TTC-AGA-CG-5' was prepared using a DNA synthesizer. Three separate lumole batches of each oligonucleotide were made and each was attached to a solid support and fully protected by a dimethoxytrityl radical. The dimethoxytrityl protecting group was removed from the 5'-terminus and 1 was attached to the 19-unit chain without the DNA synthesizer, but using the same reagents and conditions the machine typically employs.

The product of this process, after removal from the support, was an oligonucleotide with a 5'-(-aminoallyl-5'-(4,4'-dimethoxytrityl)-2'-deoxy-uridine unit at the C-5' end, viz.,

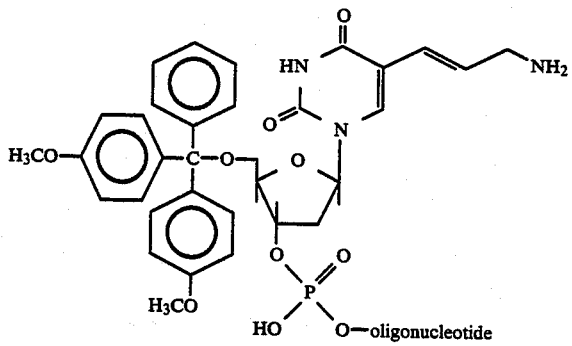

The product polynucleotides were lastly de-tritylated with brief exposure to a 3% trichloracetic acid then purified by polyacrylamide gel electrophoresis.

The polynucleotide HBl9A' is a unit polynucleotide corresponding to a portion of human DNA which codes for the polypeptide beta hemoglobin, specifically that region of the DNA wherein lies the mutation which manifests itself in the formation of sickle-cell hemoglobin and the genetic disorder known as sickle cell anemia.

Infrared (IR) spectra were otained as solutions in $CHCl_3$ unless otherwise noted. The 1602 $cm^{-1}$ band of polystyrene film was used as an external calibration standard.

Proton magnetic resonance ($^1H$ NMR) spectra were obtained in $CDCl_3$ solution unless otherwise noted. Chemical shifts are reported in parts per million downfield from the internal standard tetramethylsilane, unless otherwise noted.

Carbon-13 magnetic resonance ($^{13}C$ NMR) spectra were obtained in $CDCl_3$ solution unless otherwise noted. Carbon shifts are reported in parts per million downfield from the internal standard tetramethylsilane, unless otherwise noted.

Phosphorous-31 magnetic resonance ($^{31}PNMR$) spectra were obtained in $CDCl_3$ solution unless otherwise noted. Phosphorous shifts are reported in parts per million downfield from an external aqueous 15% $H_3PO_4$ standard.

Thin layer chromatograph (TLC) was performed using silica gel 60F-254 plates from E. Merck. Column chromatography was performed using E. Merck Silica Gel 60 (70-230 mesh).

5-Trifluoroacetamidoallyl-2'deoxyuridine (8)

A suspension of 5-chloromercuri-2'-deoxyuridine (5) (Bergstrom and Ruth, supra) (5.56 g; 12 nmol) in HPLC (high performance liquid chromatography) grade methanol 120 ml) was maintained under an inert gas atmosphere at ambient temperature and treated wth 3-trifluoro-acetamido-1-propene (7) (Pailer and Hubsch, supra) (7.33 g; 48 mmol; 4 equivalents), and $K_2PdCl_4$ (4.28 g; 1.1 equivalents). The reaction gradually became black and was stirred for 22 hours. The mixture was treated with $H_2S$ gas for several minutes, then filtered through Celite, rinsed with methanol and evaporated to dryness under reduced pressure from a 80° C. bath to give a crude semi-solid residue (7.0 g). The residue was chromatographed on a silica gel column developed with $CH_2Cl_2$: MeOH (5:1). The band which stained a blue color with modified p-anisaldehyde reagent (Egon Stahl, *Thin Layer Chromatograph*, 2nd Edition, Springer-Verlong, N.Y., 857 (1969)) and had an $R_f=0.51$ ($CH_3CN$: MeOH 3:1) was collected and evaporated to dryness in vacuo to give a colorless form. The product was crystallized from a minimum of methanol, filtered, washed with cold $CHCl_3$:MeOH (3:1) and vacuum dried. The mother liquor was worked for a secon crop-total yield 1.01 g (22%). A recrystallization from MeOH produced the title compound (8) as analytically pure tiny white needles with mp=183°-4° after drying in vacuo (<1.0 torr) at 64° C. overnight. IR (KBr) $cm^{-1}$ 3420, 3260, 1718, 1683 (br), 1560, 1478, 1283, 1190, 1102, 1061, 980, 788, 763, 737; $^1H$ NMR (DMSO-$d^6$) (Ref. DMSO-$d^6$) 2.13 (d of d, J=6 Hz, 2H), 3.59 (br s, 2H), 3.70-3.97 (m, 3H), 4.25 br s, 1H), 5.06 (br m, 1H), 5.20 (br m, 1H), 6.05-6.65 ($m_6$, 4H), 8.01 (s, 1H), 9.60 (br s, 1H); $^{13}NMR$ (SMSO-$d^6$) (Ref. DMSO-d) ppm 162.05, 155.29, 149.50, 138.05, 124.33, 124.14, 109.96, 87.53, 84.47, 70.23, 61.12, 39.93; $(\alpha)_D=+8.01°$ (c=0.87, MeOH).

Anal. Calculated for $C_{14}H_{16}N_3O_6F_3$: C, 44.33; H, 4.25; N, 11.08 Found: C, 44.19; H, 4.10; N, 10.93
5'-Trifluoroacetamidoallyl-5'-0-(4,4'-dimethoxytrityl)-2'deoxyuridine (9)

A solution of 8 (0.60 g; 1.58 mmol) in anhydrous pyridine (8 ml) was maintained under an inert gas atmosphere and treated at ambient temperature with 4,4'-dimethoxytrityl chloride (0.67 g; 1.25 equivalents). After stirring for 18 hours the reaction was poured into ice water (70 ml) with vigorous shaking. On standing one-third of an hour at 0° C., a gummy solid was separated out, leaving a nearly clear solution which was decanted. The solid was washed once with $H_2O$ (5 ml) then taken up in $CH_3Cl_2$, washed once with brine (5 ml) then the $CH_2Cl_2$ solution was dried over $K_2CO_3$, filtered and evaporated to dryness in vacuo to give a brownish foam. The crude product was purified by flash chromatography (Still et al, supra) on a column of silica gel (Merck, Rahway, NJ., U.S.A., Grade 60, 230-400 mesh, 60A) (75 g) developed with 4.0% MeOH in $CHCl_3$ solvent (1.0 liter). Fractions of ca. 20 ml each were collected in tubes containing pyridine (10 μl) to inhibit deprotection of the 5'hydroxyl. Fractions containing the major product band ($R_f=0.29$; MeOH: $CHCl_3$ 7.93) were combined, filtered and evaporated to dryness in vacuo to give 9 (0.91 g; 85%) as a slightly yellowish foam. A fraction from the center of the elution band was freed of solvent, taken up in ethyl acetate (EtoAc), treated with Norit 211, filtered through Celite and evaporated to dryness under high vacuum (<1.0 torr) at 64° C. overnight to afford the analytical sample as a colorless foam with mp=105°-110° C. (dec.). IR (CHCl$_3$)cm$^{-1}$ 3370, 2920, 1715, 1695, 1618, 1515, 1470, 1260, 1182, 1045, 842; $^1$H NMR (CDCl$_3$) 2.38 (br m, 2H), 3.25-3.75 (m, 5H), 3.75 (s, 6H), 4.10 (br m, 1H), 4.60 (br s, 1H), 5.39 (d, J=16 Hz, 1H), 6.10-6.55 (m, 2H), 6.70-6.95 (m, 5H, 7.15-7.45 (m, 10H), 7.84 (s, 1H); $^{13}$C NMR (CDCl$_3$) (Ref. CDCl$_3$) ppm 162.31, 158.74, 157.70, 156.01, 149.70, 144.04, 137.88, 135.65, 135.52, 130.12, 128.11, 127.26, 125.05, 113.48, 111.33, 86.94, 86.68, 85.25, 72.18, 63.60, 55.34, 42.66, 41.42.

Anal. Calculated for $C_{35}H_{34}N_3O_8F_3$: C, 61.67; H, 5.03; N, 6.16 Found: C, 61.47; H, 5.19; N, 5.95

5-Trifluoroacetamidoallyl-5'O-(4,4'-dimethoxytrityl)-2'deoxyuridine-3'-O-(N,N-diisopropylaminomethoxy phospine (1)

A solution of 9 (0.34 g; 0.5 mmol) in anhydrous CH$_2$Cl$_2$ (1.5 ml) maintained under an argon atmosphere at ambient temperature was treated first with anhydrous, diisopropylethylamine (0.35 ml; 0.259 g; 2 mmol; 4 equivalents) then dropwise, over 1 minute with N, N-diisopropylaminomethoxy-chlorophosphine (see McBride et al, supra) (10) (0.9 ml; ca 0.2 g; 2.2 equivalents). The resultant colorless solution was stirred for 20 minutes then transferred with ethylacetate (EtOAc) (20ml). EtOAc was previously washed with saturated aq NaHCO$_3$, then brine) to a separatory funnel, washed four times with brine (35 ml each), dried over Na$_2$SO$_4$, filtered and evaporated to dryness in vacuo to give a colorless glass (0.51 g.). This crude product was taken up in anhydrous benzene (2 ml) and precipitated into rapidly stirred anhydrous pentane (60 ml) at −78° C. under an argon atmosphere. The resulting suspension was filtered, washed with −78° C. pentane and vacuum dried at <1 torr over KOH overnight to obtain the title compound (1) (0.38 g; 93%) as a white amorphous powder. IR (CHCl$_3$) cm$^{-1}$ 2965, 1722, 1698, 1618, 1518, 1470, 1262, 1185, 1045, 988, 842; $^1$H NMR (CD$_2$Cl$_2$) 0.95-1.30 (m, 12H), 2.20-2.60 (m, 2H), 3.24 and 3.37 (d of d, J=13 Hz, 3H) (P—O—CH$_3$), 3.20-3.80 (m, 6H), 3.75 (s, 6H), 4.17 (br m, 1H), 4.68 (v br m, 1H), 5.42 (d, J=16 Hz, 1H), 6.15-6.55 (m,3H), 6.75-6.95 (m, 4H), 7.20-7.50 (m, 10H) 7.79 (s, 1H); $^{13}$C NMR (CD$_2$Cl$_2$) (Ref. CD$_2$Cl$_2$) ppm 162.40, 159.21, 157.78, 149.78, 144.71, 138.34, 136.00, 130.53, 128.71, 128.45, 127.54, 125.66, 125.27, 113.82, 111.48, 87.23, 86.31, 85.60, 55.75, 43.78, 43.20, 42.94, 24.29, 24.60, $^{31}$ PNMR (CD$_2$Cl$_2$) ppm 149.30, 148.87, 14.11 (approximately 12% impurity), 8.18 (approximately 4% impurity).

Attachment of 1 to Oligonucleotides

The 19-unit oligonucleotides were synthesized using an Applied Bio-Systems Model 380A DNA Synthesizer on control pore glass solid support. Immediately prior to attaching 1 to the 5' end of the oligomer, the 5'-O-(4,4'-dimethoxytrityl) protecting group was cleaved on the machine with 3% CCl$_3$CO$_2$H in CH$_2$Cl$_2$ for 90 seconds. The support-bound 5'deprotected oligomer was washed with CH$_3$CH and dried in an argon stream. Subsequent steps were performed without the machine, but using the same chemistry;

1. The support-bound oligomer was removed from the container (column) used for automated synthesis and transferred to dry septum-cap vial under an argon atmosphere.
2. The bound oligomer was treated with a 20-30 fold excess of 0.5 M 1 H-tetrazole in anhydrous CH$_3$CN. It was incubated for 30 minutes with gentle agitation
3. Reagents were pipetted-off and the bound oligomer was washed with three portions of CH$_3$CN.
4. The solid support containing the bound oligomer was treated with an excess of I$_2$H$_2$O-Lutidine-THF (0.1 M: 1:10:40) and agitated for 15 minutes.
5. Reagents were pipetted and the bound oligomer was washed with four portions of CH$_3$CN.
6. The solid support containing the bound oligomer was washed with an excess of thiophenol-triethylamine-dioxane for 60 minutes.
7. Reagents were pipetted off and the bound oligomer was washed with four portions of MeOH.
8. The solid support containing the bound oligomer was treated with concentrated aqueous NH$_4$OH for 2 hours at ambient temperature (this removes protected oligonucleotide from the support).
9. To remove all protecting groups, the oligonucleotide was treated with concentrated aqueous NH$_4$OH and heated at 50° C. overnight (this removes all protecting groups, except the dimethoxytrityl).
10. The support was filtered-off and the filtrate was evaporated to dryness to obtain crude oligonucleotide.

The above ten steps were repeated for all batches of support-bound oligonucleotide. Treatment of a portion of each on a silica gel TLC plate with 3% CCl$_3$CO$_2$H in CH$_2$Cl$_2$ produced the orange-red color of dimethoxytrityl cation indicating the successful incorporation of 1 into the oligonucleotides.

One bath of the modified HB19A' oligonucleotide was detrylated with 3% CCl$_3$CO$_2$H in CH$_2$Cl$_2$ and purified by electrophoresis on polyacrylamide gel.

EXAMPLE 8b

THE REACTION OF A SPECIFIC OLIGONUCLEOTIDE WITH N-HYDROXSUCCINIMIDO BITOIN (NHS-BIOTIN)

Two micrograms of 19A' amine or 19S'-amine from Examples 8a were dissolved in 20 microliters of 10 mM borate buffer pH 8.16. To this, 5 microliters of a freshly prepared DMF solution of N-hydroxysuccinimido biotin (10 mg/ml) purchased from Pierce Chemical Co., Rockford, Ill. U.S.A., were added. The reaction was allowed to proceed at room temperature for 16 hours. After the reaction, the solvent was evaporated under reduced pressure.

EXAMPLE 8c

THE SEPARATION OF NHS BIOTIN REACTED 19A' FROM THE REACTION MIXTURE

HPLC separation is conducted on a Brownlee RP300 guard column coupled to a Synchropack RPP 4.1×10 cm (Synchrom, Linden, Ind., U.S.A.) column at ambient temperature with a gradient of 0.1M triethylammonium acetate pH 7 to 0.1M triethylammonium acetate pH 7, 50% acetonitrile is run over a period of 10–120 minutes depending on the sample. The detector is set at 254 nm and full scale is 0.15 absorbance unit. In order to determine the location of the derivatized oligonucleotide product, a blank run is carried out with the reaction mixture without the oligonucleotide. A new peak appears after adding the oligonucleotide and corresponds to the reaction product. After the product is separated and collected in a fraction collector, the product is analyzed by gel electrophoresis and from the next run an analytical determination of the proper peak is found to be not necessary. The oligonucleotide is then evaporated to dryness under reduced pressure.

EXAMPLE 8d

Hybridization and Detection of a Hybridized Oligonucleotide

For demonstration purposes purified blood DNA is immobilized on nitrocellulose paper, prehybridized as in Example 4, hybridized with biotinylated oligonucleotide product of Example 8c under conditions as described in Conner et al, *Proc. Natl. Acad. Sci.*, 80, 278 (1983) and detected by chemiluminescent method as in Example 3.

Chemiluminescence in Examples 3-7 and 8d were determined by photoradiography means on a "POLAROID" film holder.

The film was exposed when the light emitter probe and the film were in the casette separated only by a thin transparent piece of solid material, e.g., "SARAN WRAP" transparent fiber, or a flat side of a microtiter plate. It will be understood that the specification and examples are illustrative, but not limitative of the present invention and that other embodiments within the spirit and scope of the invention will suggest themselves to those skilled in the art.

What is claimed is:

1. A method for determining a particular single stranded polynucleotide sequence in a test medium, comprising the steps of:
   (a) immobilizing on a solid support single stranded nucleic acids in the test medium,
   (b) contacting the immobilized nucleic acids with a polynucleotide probe having a base sequence substantially complementary to the sequence to be determined and said contacting being under conditions favorable to hybridization between the probe and the sequence to be determined, wherein the probe is labeled with a chemiluminescence enhancer,
   (c) separating the immobilized hybrids from the unhybridized probe,
   (d) initiating a chemiluminescent reaction by contacting the separated, labeled, immobilized hybrids with an oxidant, a 2,3-dihydro-1,4-phthalazinedione chemiluminescence precursor, and a peroxidase enzyme,
   (e) detecting the resulting light emission, and
   (f) relating the amount of emitted light to the amount of the single stranded polynucleotide sequence,
   the chemiluminescence enhancer being selected from the group consisting of luciferin and dehydroluciferin and wherein the chemiluminescent precursor is a 2,3-dihydro-1,4-phthalazinedione of the formula

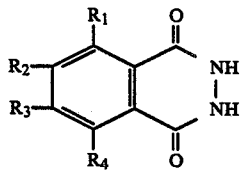

wherein $R_1$ is amino, and $R_2$, $R_3$ and $R_4$ are all H and wherein $R_1$ is amino and each of $R_2$, $R_3$ and $R_4$ is unsubstituted $C_1$-$C_6$-alkyl or alkenyl or $C_1C_6$-alkyl or alkenyl substituted by a substituent selected from the group consisting of chlorine, fluorine, bromine, iodine, hydroxy, carboxy, nitro, cyano and thiol; hydroxyl; $C_1$-$C_6$-alkoxy; carboxyl or amino or $R_2$ is an amino or substituted amino and each of $R_1$, $R_3$ and $R_4$ is H, unsubstituted $C_1$-$C_6$-alkyl or alkenyl or $C_1$-$C_6$-alkyl or alkenyl substituted by a substituent selected from the group consisting of chlorine, fluorine, bromine, iodine, hydroxy, carboxy, nitro, cyano and thiol; hydroxyl; $C_1$-$C_6$-alkoxy or carboxyl, amino, or $R_1$ and $R_2$ together with the ring carbon atoms they are bonded to form a fused benz ring which is substituted with an amino group or a substituted amino group, said substituted amino group being substituted by a substituent selected from the group consisting of carboxy, $C_1$-$C_{10}$ alkyl and $C_2$-$C_{10}$ alkenyl, and each of $R_3$ and $R_4$ is H, unsubstituted $C_1$-$C_6$-alkyl or alkenyl or $C_1$-$C_6$-alkyl or alkenyl substituted by a substituent slected from the group cossisting of chlorine, fluorine, bromine, iodine, hydroyy, carboxy, nitro, cyano and thiol; hydroxyl; $C_1$-$C_6$-alkoxy; carboxyl or amino, said hydroxyl being unsubstituted or substituted by a substituent selected from the group consisting of $C_1$-$C_{10}$ alkyl and $C_2$-$C_{10}$ alkenyl.

2. A nucleic acid-containing composition capable of participating in an enhanced chemiluminescent reaction comprising (i) a defined nucleic acid sequence, said sequence being covlently linked by a photoreactive intercalator to, (ii) a peroxidase enzyme and (iii) a chemiluminescence precursor, wherein said chemiluminescence precursor is a 2,3-dihydro-1,4-phthalazinedione of the formula

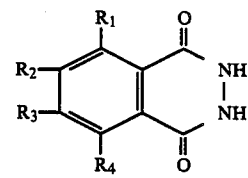

wherein $R_1$ is amino, and $R_2$, $R_3$ and $R_4$ are all H and wherein $R_1$ is amino and each of $R_2$, $R_3$ and $R_4$ is unsubstituted $C_1$-$C_6$-alkyl or alkenyl or $C_1$-$C_6$-alkyl or alkenyl substituted by a substituent selected from the group consisting of chlorine, fluroine, bromine, iodine, hydroxy, carboxy, nitro, cyano and thiol; hydroxyl; $C_1$-$C_6$-alkoxy carboxyl or amino or $R_2$ is an amino or substituted amino and each of $R_1$, $R_3$ and $R_4$ is H, unsubstituted $C_1$-$C_6$-alkyl or alkenyl or $C_1$-$C_6$-alkyl or alkenyl substituted by a substituent selected from the group consisting of chlorine, fluorine, bromine, iodine, hydroxy, carboxy, nitro, cyano and thiol; hydroxyl; $C_1$-$C_6$-alkoxy or carboxyl, amino, or $R_1$ and $R_2$ together with the ring carbon atoms they are bonded to form a fused benz ring which is substituted with an amino group or a substituted amino group, said substituted amino group being substituted by a substituent selected from the group consisting of carboxy, $C_1$-$C_{10}$ alkyl and $C_2$-$C_{10}$ alkenyl, and each of $R_3$ and $R_4$ is H, unsubstituted $C_1$-$C_6$-alkyl or alkenyl or $C_1$-$C_6$-alkyl or alkenyl substituted by a substituent selected from the group consisting of chlorine, fluorine, bromine, iodine, hydroxy, carboxy, nitro, cyano and thiol; hydroxyl; $C_1$-$C_6$-alkoxy; carboxyl or amino, said hydroxyl being unsubstituted or substituted by a substituent selected from the group consisting of $C_1$-$C_{10}$ alkyl and $C_2$-$C_{10}$ alkenyl, and said enhancer being selected from the group consisting of luciferin and dehydroluciferin.

3. A nucleic acid-containing composition according to claim 2, wherein said composition exists as a homogeneous mixture.

4. A nucleic acid-containing composition according to claim 2, wherein said chemiluminescence precursor is selected from the group consisting of luminol and isoluminol.

5. A nucleic acid-containing composition according to claim 2 wherein said enzyme enzyme is selected from the group consisting of horseradish peroxidase, microperoxidase and lactoperoxidase.

* * * * *

UNITED STATES PATENT AND TRADEMARK OFFICE
CERTIFICATE OF CORRECTION

PATENT NO. : 4,794,073
DATED : Dec. 27, 1988
INVENTOR(S) : Dattagupta et al.

It is certified that error appears in the above-identified patent and that said Letters Patent is hereby corrected as shown below:

| | |
|---|---|
| Col. 21, line 44 | Delete "lug" and substitute --1 $\mu$g-- |
| Col. 30, line 50 | Insert --(10 ml)-- after "CH$_3$Cl$_2$" |
| Col. 34, line 29 | Insert --a chemiluminescence enhancer-- after "to" |
| Col. 36, line 4 | Delete "enzyme" in first instance and substitute --peroxidase-- |

Signed and Sealed this

Ninth Day of January, 1990

Attest:

JEFFREY M. SAMUELS

Attesting Officer     Acting Commissioner of Patents and Trademarks